(12) United States Patent
Magnani et al.

(10) Patent No.: US 7,517,980 B2
(45) Date of Patent: Apr. 14, 2009

(54) GLYCOMIMETRIC INHIBITORS OF THE PA-IL LECTIN, PA-IIL LECTIN OR BOTH THE LECTINS FROM PSEUDOMONAS

(75) Inventors: John L. Magnani, Gaithersburg, MD (US); John T. Patton, Jr., Gaithersburg, MD (US); Arun K. Sarkar, North Potomac, MD (US)

(73) Assignee: GlycoMimetics, Inc., Gaithersburg, MD (US)

( * ) Notice: Subject to any disclaimer, the term of this patent is extended or adjusted under 35 U.S.C. 154(b) by 233 days.

(21) Appl. No.: 11/501,464

(22) Filed: Aug. 8, 2006

(65) Prior Publication Data

US 2007/0037775 A1 Feb. 15, 2007

Related U.S. Application Data

(60) Provisional application No. 60/810,190, filed on Jun. 1, 2006, provisional application No. 60/706,546, filed on Aug. 9, 2005.

(51) Int. Cl.
*C07H 3/06* (2006.01)
*A61K 31/702* (2006.01)
*C07H 3/02* (2006.01)

(52) U.S. Cl. .................... 536/123; 514/53; 514/54; 536/123.13

(58) Field of Classification Search ............... 536/123; 514/53
See application file for complete search history.

(56) References Cited

U.S. PATENT DOCUMENTS

| | | | |
|---|---|---|---|
| 4,471,057 A | 9/1984 | Koprowski et al. ........... 436/518 |
| 4,851,511 A | 7/1989 | Hakomori et al. ........... 530/387 |
| 4,859,769 A | 8/1989 | Karlsson et al. ................ 536/53 |
| 4,876,199 A | 10/1989 | Hakomori ................... 530/387 |
| 4,925,796 A | 5/1990 | Bergh et al. .................... 435/97 |
| 4,946,830 A | 8/1990 | Pulverer et al. ............... 514/23 |
| 5,143,712 A | 9/1992 | Brandley et al. .............. 424/1.1 |
| 5,151,360 A | 9/1992 | Handa et al. ............. 435/240.2 |
| 5,211,937 A | 5/1993 | Brandley et al. .............. 424/1.1 |
| 5,268,364 A | 12/1993 | Kojima et al. ................. 514/25 |
| 5,304,640 A | 4/1994 | Lasky et al. ................ 536/23.5 |
| 5,352,670 A | 10/1994 | Venot et al. .................... 514/54 |
| 5,369,096 A | 11/1994 | Yamada et al. ................ 514/61 |
| 5,412,123 A | 5/1995 | Rao et al. ..................... 552/290 |
| 5,444,050 A | 8/1995 | Kogan et al. ................... 514/25 |
| 5,464,778 A | 11/1995 | Cummings et al. ........... 436/503 |
| 5,464,815 A | 11/1995 | Chamow et al. ................. 514/8 |
| 5,470,843 A | 11/1995 | Stahl et al. ..................... 514/61 |
| 5,484,891 A | 1/1996 | Lasky et al. ............... 530/387.3 |
| 5,486,536 A | 1/1996 | Ward et al. ................... 514/460 |
| 5,519,008 A | 5/1996 | Rao et al. ...................... 514/26 |
| 5,527,785 A | 6/1996 | Bevilacqua et al. ........... 514/56 |
| 5,538,724 A | 7/1996 | Butcher et al. ............ 424/152.1 |
| 5,559,103 A | 9/1996 | Gaeta et al. .................... 514/54 |
| 5,576,305 A | 11/1996 | Ratcliffe ....................... 514/25 |
| 5,580,858 A | 12/1996 | Ippolito et al. ................ 514/25 |
| 5,580,862 A | 12/1996 | Rosen et al. ................... 514/61 |
| 5,589,465 A | 12/1996 | Ishida et al. ................... 514/25 |
| 5,604,207 A | 2/1997 | DeFrees et al. ................ 514/25 |
| 5,618,785 A | 4/1997 | Heavner et al. ................ 514/2 |
| 5,622,937 A | 4/1997 | Kogan et al. ................... 514/25 |
| 5,639,734 A | 6/1997 | Esko et al. ..................... 514/25 |
| 5,646,123 A | 7/1997 | Ippolito et al. ................ 514/25 |
| 5,646,248 A | 7/1997 | Sawada et al. ............... 530/350 |
| 5,648,344 A | 7/1997 | Brandley et al. .............. 514/61 |
| 5,654,282 A | 8/1997 | Tang et al. ..................... 514/25 |
| 5,654,412 A | 8/1997 | Srivastava et al. ........... 536/18.5 |
| 5,658,880 A | 8/1997 | Dasgupta et al. ............... 514/8 |
| 5,663,151 A | 9/1997 | Martel et al. ................... 514/25 |
| 5,679,321 A | 10/1997 | Dasgupta et al. ............. 424/9.1 |
| 5,679,644 A | 10/1997 | Rao et al. ...................... 514/26 |
| 5,686,426 A | 11/1997 | Martel et al. ................... 514/25 |
| 5,693,621 A | 12/1997 | Toepfer et al. ................ 514/25 |
| 5,695,752 A | 12/1997 | Rosen et al. ............. 424/94.61 |
| 5,710,023 A | 1/1998 | Collins et al. .............. 435/69.1 |
| 5,710,123 A | 1/1998 | Heavner et al. ................ 514/2 |

(Continued)

FOREIGN PATENT DOCUMENTS

EP 319253 A2 6/1989

(Continued)

OTHER PUBLICATIONS

Acord, J. et al., "A rapid microplate method for quantifying inhibition of bacterial adhesion to eukaryotic cells," *Journal of Microbiological Methods* 60: 55-62, 2005.

(Continued)

*Primary Examiner*—Shaojia Anna Jiang
*Assistant Examiner*—Jonathan S Lau
(74) *Attorney, Agent, or Firm*—Seed IP Law Group PLLC

(57) ABSTRACT

Compositions and methods are provided related to *Pseudomonas* bacteria. The compositions and methods may be used for diagnosis and therapy of medical conditions involving infection with *Pseudomonas* bacteria. Such infections include *Pseudomonas aeruginosa* in the lungs of patients with cystic fibrosis. A compound useful in the present methods may be used in combination with a therapeutic agent or may be linked to a therapeutic agent. *Pseudomonas* bacteria may be inhibited by blocking colonization, inhibiting virulence factors, arresting growth or killing the bacteria.

2 Claims, 10 Drawing Sheets

U.S. PATENT DOCUMENTS

| | | |
|---|---|---|
| 5,723,583 A | 3/1998 | Seed et al. ............... 530/387.3 |
| 5,728,685 A | 3/1998 | Abbas et al. .................. 514/53 |
| 5,739,300 A | 4/1998 | Toepfer et al. ............... 536/4.1 |
| 5,747,463 A | 5/1998 | Marinier et al. ............... 514/25 |
| 5,750,508 A | 5/1998 | Dasgupta et al. .............. 514/25 |
| 5,753,617 A | 5/1998 | Heavner et al. ................. 514/9 |
| 5,753,631 A | 5/1998 | Paulson et al. ................ 514/25 |
| 5,763,413 A | 6/1998 | Numata et al. ................ 514/25 |
| 5,763,582 A | 6/1998 | Rao et al. ....................... 536/5 |
| 5,789,385 A | 8/1998 | Anderson et al. ............. 514/25 |
| 5,789,573 A | 8/1998 | Baker et al. ................ 536/24.5 |
| 5,795,958 A | 8/1998 | Rao et al. ................... 530/331 |
| 5,811,404 A | 9/1998 | De Frees et al. .............. 514/25 |
| 5,811,405 A | 9/1998 | Toepfer et al. ................ 514/25 |
| 5,817,742 A | 10/1998 | Toepfer et al. .............. 528/328 |
| 5,827,817 A | 10/1998 | Larsen et al. ................... 514/2 |
| 5,827,837 A | 10/1998 | Bevilacqua et al. .......... 514/103 |
| 5,830,871 A | 11/1998 | Wong et al. ................... 514/23 |
| 5,837,689 A | 11/1998 | Anderson et al. ............. 514/25 |
| 5,837,690 A | 11/1998 | Rao et al. ...................... 514/26 |
| 5,840,679 A | 11/1998 | Larsen et al. ................... 514/8 |
| 5,854,218 A | 12/1998 | DeFrees ....................... 514/25 |
| 5,858,983 A | 1/1999 | Seed et al. .................... 514/23 |
| 5,858,994 A | 1/1999 | Kretzschmar et al. ......... 514/62 |
| 5,880,091 A | 3/1999 | Cummings et al. .............. 514/8 |
| 5,916,910 A | 6/1999 | Lai ............................. 514/423 |
| 5,919,768 A | 7/1999 | Kogan et al. .................. 514/25 |
| 5,919,769 A | 7/1999 | Tsukida et al. ................ 514/25 |
| 5,962,422 A | 10/1999 | Nagy et al. .................... 514/25 |
| 5,976,540 A | 11/1999 | Rittershaus et al. ....... 424/184.1 |
| 5,977,080 A | 11/1999 | Rosen et al. .................. 514/25 |
| 5,985,852 A | 11/1999 | Nagy et al. .................... 514/54 |
| 5,994,402 A | 11/1999 | Rotstein et al. ............. 514/547 |
| 6,001,819 A | 12/1999 | Simon et al. .................. 514/54 |
| 6,001,988 A | 12/1999 | Parma et al. ............... 536/24.3 |
| 6,033,665 A | 3/2000 | Yednock et al. .......... 424/130.1 |
| 6,037,333 A | 3/2000 | Panjwani ...................... 514/62 |
| 6,110,897 A | 8/2000 | Unverzagt et al. ............. 514/25 |
| 6,111,065 A | 8/2000 | Heavner et al. ............. 530/300 |
| 6,120,751 A | 9/2000 | Unger ........................ 424/9.51 |
| 6,121,233 A | 9/2000 | Magnani et al. ................. 514/8 |
| 6,124,267 A | 9/2000 | McEver et al. ................ 514/25 |
| 6,133,239 A | 10/2000 | Handa et al. .................. 514/25 |
| 6,133,240 A | 10/2000 | Taylor et al. .................. 514/25 |
| 6,136,790 A | 10/2000 | Toepfer et al. ................ 514/25 |
| 6,169,077 B1 | 1/2001 | Oehrlein ....................... 514/25 |
| 6,177,547 B1 | 1/2001 | Cummings et al. ..... 530/388.22 |
| 6,187,754 B1 | 2/2001 | Oehrlein ....................... 514/25 |
| 6,193,973 B1 | 2/2001 | Tuttle ......................... 424/195.1 |
| 6,193,979 B1 | 2/2001 | Rittershaus et al. .... 424/195.11 |
| 6,197,752 B1 | 3/2001 | Schmidt et al. ............... 514/23 |
| 6,225,071 B1 | 5/2001 | Cummings et al. ......... 435/7.24 |
| 6,235,309 B1 | 5/2001 | Nagy et al. .................. 424/450 |
| 6,280,932 B1 | 8/2001 | Parma et al. .................... 435/6 |
| 6,309,639 B1 | 10/2001 | Cummings et al. ......... 434/143.1 |
| 6,387,884 B1 | 5/2002 | Magnani et al. ............... 514/25 |
| 6,391,857 B1 | 5/2002 | Magnani et al. ............... 514/25 |
| 6,407,135 B1 | 6/2002 | Lai et al. ..................... 514/423 |
| 6,465,434 B1 | 10/2002 | Magnani et al. ............... 514/23 |
| 6,492,332 B1 | 12/2002 | Demopulos et al. ........... 514/12 |
| 6,503,885 B1 | 1/2003 | Kiso et al. ..................... 514/25 |
| 6,528,487 B1 | 3/2003 | Heavner et al. ............... 514/13 |
| 2001/0046970 A1 | 11/2001 | Nagy et al. .................... 514/53 |
| 2001/0051370 A1 | 12/2001 | Bistrup et al. ................ 435/193 |
| 2002/0026033 A1 | 2/2002 | Cummings et al. .......... 530/322 |
| 2002/0028205 A1 | 3/2002 | Holgersson et al. ....... 424/184.1 |
| 2002/0031508 A1 | 3/2002 | Wagner et al. ........... 424/94.63 |
| 2002/0040008 A1 | 4/2002 | Wagner et al. ................ 514/41 |
| 2002/0132220 A1 | 9/2002 | Berens et al. ................ 435/1.1 |
| 2002/0164336 A1 | 11/2002 | Harrison et al. ........... 424/146.1 |
| 2002/0164748 A1 | 11/2002 | Bistrup et al. ................ 435/193 |
| 2002/0168366 A1 | 11/2002 | Stewart et al. ........... 424/146.1 |
| 2003/0012787 A1 | 1/2003 | Ashkenazi et al. ....... 424/145.1 |
| 2003/0012790 A1 | 1/2003 | Ashkenazi et al. ....... 424/178.1 |
| 2003/0018181 A1 | 1/2003 | Larsen et al. ............... 536/23.4 |
| 2003/0039683 A1 | 2/2003 | Cantrell et al. .............. 424/450 |

FOREIGN PATENT DOCUMENTS

| | | | |
|---|---|---|---|
| EP | | 381310 A1 | 8/1990 |
| EP | | 408859 B2 | 8/1995 |
| EP | | 671407 A2 | 9/1995 |
| WO | WO 90/13300 | | 11/1990 |
| WO | WO 91/19502 | | 12/1991 |
| WO | WO 92/01718 | | 2/1992 |
| WO | WO 92/07572 | | 5/1992 |
| WO | WO 94/26760 | | 11/1994 |
| WO | WO 94/29477 | | 12/1994 |
| WO | WO 95/03059 | | 2/1995 |
| WO | WO 95/00527 | * | 11/1995 |
| WO | WO 95/29681 | | 11/1995 |
| WO | WO 96/20204 | | 7/1996 |
| WO | WO 96/25418 | | 8/1996 |
| WO | WO 96/26950 | | 9/1996 |
| WO | WO 97/01335 | | 1/1997 |
| WO | WO 97/01569 | | 1/1997 |
| WO | WO 97/14707 | | 4/1997 |
| WO | WO 97/28173 | | 8/1997 |
| WO | WO 97/28174 | | 8/1997 |
| WO | WO 98/06730 | | 2/1998 |
| WO | WO 99/42130 | | 8/1999 |
| WO | WO 99/43353 | | 9/1999 |
| WO | WO 99/43356 | | 9/1999 |
| WO | WO 02/22820 | | 3/2002 |
| WO | WO 02/062810 | | 8/2002 |
| WO | WO 03/097658 | | 11/2003 |
| WO | WO 2004/004636 | | 1/2004 |
| WO | WO 2004/058304 | | 7/2004 |
| WO | WO 2006/127906 | | 11/2006 |

OTHER PUBLICATIONS

Perret, S. et al. "Structural basis for the interaction between human milk oligosaccharides and the bacterial lectin PA-IIL of *Pseudomonas aeruginosa, "Biochem. J. 389*: 325-332, 2005.

Abraham, W.M. et al., "Selectin Blockade Prevents Antigen-induced Late Bronchial Response and Airway Hyperresponsiveness in Allergic Sheep," *Am J. Respir Crit Care Med. 159*: 1205-1214, 1999.

Baeckström et al., "Purification and Characterization of a Membrane-bound and a Secreted Mucin-type Glycoprotein Carrying the Carcinoma-associated Sialyl-Le[a] Epitope on Distinct Core Proteins," *J. Biol. Chem. 266*(32):21537-21547, 1991.

Bänteli, R. et al., "Potent E-Selectin Antagonist," *Helvectica Chimica Acta 83*(11): 2893-2907, 2000.

Berg et al., "A Carbohydrate Domain Ceommon to Both Sialyl Le[a] and Sialyl Le[x] Is Recognized by the Endothelial Cell Leukocyte Adhesion Molecule ELAM-1," *J. Biol. Chem. 266*(23):14869-14872, 1991.

Berg et al., "The Cutaneous Lymphocyte Antigen Is a Skin Lymphocyte Homing Receptor for the Vascular Lectin Endothelial Cell-Leukocyte Adhesion Molecular 1," *J. Exp. Med. 174*:1461-1466, 1991.

Bird and Kimber, "Oligosaccharides Containing Fucose Linked α(1-3) and α(1-4) to *N*-Acetylglucosamine Cause Decompaction of Mouse Morulae," *Devel. Biol. 104*:449-460, 1984.

Bjercke, J., "Rational Design and Synthesis of Oligosaccharide Mimetics: Selectin Antagonists as Cell Adhesion Inhibitors," *Abstracts of Papers, 210th ACS National Meeting*, American Chemical Society, Chicago, IL, Aug. 20-24, 1995, MEDI-18.

Bowen et al., "Characterization of a Human Homologue of the Murine Peripheral Lymph Node Homing Receptor," *Journal of Cell Biology 109*:421-427, 1989.

Brandley et al., "Carbohydrate Ligands of LEC Cell Adhesion Molecules," *Cell 63*:861-863, 1990.

Broquet et al., "Effect of Desipramine on a Glycoprotein Sialytransferase Activity in C6 Cultured Glioma Cells," *J. Neurochem.* 54:388-394, 1990.

Childs et al. "High-molecular-weight glycoproteins are the major carriers of the carbohydrate differentiation antigens I, i and SSEA-1 of mouse teratocarcinoma cells," *Biochem. J.* 215:491-503, 1983.

Corral et al., "Requirements for Sialic Acid on Neutrophils in a GMP-140 (PADGEM) Mediated Adhesive Interaction with Activated Platelets," *Biochem. Biophys. Res. Commun.* 172:1349-1356, 1990.

Datta and Takayama, "Isolation and purification of trehalose 6-mono- and 6,6'-di-corynomycolates from *Cornyebacterium matruchotii*. Structural characterization of $^1$H NMR," *Carbohydrate Research* 245: 151-158, 1993.

Duijvestjin et al., "High Endothelial Differentiation in Human Lymphoid and Inflammatory Tissues Defined by Monoclonal Antibody HECA-452," *Am. J. Path.* 130:147-155, 1988.

Dupré, B. et al., "Glycomimetic Selectin Inhibitors: ($\alpha$-D-Mannopyranosyloxy)methylbiphenyls," *Bioorganic & Medicinal Chemistry Letters* 6(5): 569-572, 1996.

Edgington, "How Sweet It Is: Selectin-Mediating Drugs," *Biotechnology* 10: 383-389, 1992.

Eggens et al., "A Role of Carbohydrate-Carbohydrate Interaction in the Process of Specific Cell Recognition During Embryogenesis and Organogenesis: A Preliminary Note," *Biochem. Biophys. Res. Commun.* 158(3):913-920, 1989.

Eggens et al., "Specific Interaction between $Le^x$ and $Le^x$ Determinants. A Possible Basis for Cell Recognition in Preimplantation Embryos and in Embryonal Carcinoma Cells," *J. Biol. Chem.* 264(16):9476-9484, 1989.

Ernst and Oehrlein, "Substrate and donor specificity of glycosyl transferases," *Glycoconjugate Journal* 16: 161-170, 1999.

Fenderson et al., "A Multivalent Lacto-$N$-Fucopenataose III-Lysyllysine Conjugate Decompacts Preimplantation Mouse Embryos, While the Free Oligosaccharide is Ineffective," *J. Exp. Med.* 160:1591-1596, 1984.

Fenderson et al., "Coordinate Expression of X and Y Haptens during Murine Embryogenesis," *Devel. Biol.* 114:12-21, 1986.

Fenderson et al., "The blood group I antigen defined by monoclonal antibody C6 is a marker of early mesoderm during murine embryogenesis," *Differentiation* 38:124-133, 1988.

Fukushi et al., "Novel Fucolipidis Accumulating in Human Adenocarcinoma. II. Selective Isolation of Hybridoma Antibodies That Differentially Recognize Mono-, Di-, and Trifucosylated Type 2 Chain," *J. Biol. Chem.* 259(7):4681-4685, 1984.

Fukushi et al., "Novel Fucolipids Accumulating in Human Adenocarcinoma. III. A Hybridoma Antibody (FH6) Defining a Human Cancer-Associated Difucoganglioside ($VI^3NeuAcV^3III^3Fuc_2nLc_6$)," *J. Biol. Chem.* 259(16):10511-10517, 1984.

Gabius et al., "Endogenous Tumor Lectins: Overview and Perspectives," *Anticancer Res.* 6:573-578, 1986.

Gallatin et al., "A cell-surface molecule involved in organ-specific homing of lymphocyctes," *Nature* 304:30-34, 1983.

Gooi et al., "Stage-specific embryonic antigen involves $\alpha 1 \rightarrow 3$ fucosylated type 2 blood group chains," *Nature* 292:156-158, 1981.

Hakomori et al., "Novel Fucolipids Accumulating in Human Adenocarcinoma. I. Glycolipids With Di- or Trifucosylated Type 2 Chain," *J. Biol. Chem.* 259(7):4672-4680, 1984.

Hakomori et al., "The Hapten Structure of a Developmentally Regulated Glycolipid Antigen (SSEA-1) Isolated From Human Erythrocytes and Adenocarcinoma: A Preliminary Note," *Biochem. Biophys. Res. Commun.* 100(4):1578-1586, 1981.

Hakomori S., "Aberrant Glycosylation in Cancer Cell Membranes as Focused on Glycolipids: Overview and Perspectives," *Cancer Res.* 45:2405-2414, 1985.

Handa et al., "Selectin GMP-140 (CD62; PADGEM) Binds to Sialosyl -$Le^a$ and Sialosyl-$Le^x$, and Sulfated Glycans Moldulate this Binding," *Biochemical and Biophysical Research Communication* 181(3):1223-1230, 1991.

Hansson and Zopf, "Biosynthesis of the Cancer-associated Sialyl-$Le^a$ Antigen," *Journal of Biological Chemistry* 260(16):9388-9392, 1985.

Hasegawa et al., "Synthesis of deoxy-L-fucose-containing sialyl Lewis X ganglioside analogues," *Carbohydrate Research* 257:67-80, 1994.

Hasegawa et al., "Synthesis of sialyl Lewis X ganglioside analogues containing modified L-fucose residues," *Carbohydrate Research* 274: 165-181, 1995.

Holmes et al., "Enzymatic Basis for the Accumulation of Glycolipids with X and Dimeric X Determinants in Human Lung Cancer Cells (NCI-H69)," *J. Biol. Chem.* 260(12):7619-7627, 1985.

Huse et al., "Generation of a Large Combinatorial Library of the Immunoglobulin Repertoire in Phage Lambda," *Science* 246:1275-1281, 1989.

Hynes, R., "Integrins: A Family of Cell Surface Receptors," *Cell* 48:549-554, 1987.

Issekutz, T., "Inhibition of in Vivo Lymphocyte Migration of Inflammation and Homing to Lymphoid Tissues by the TA-2 Monoclonal Antibody. A Likely Role for VLA-4 in Vivo," *Journal of Immunology* 147:4178-4184, 1991.

Itai, S. et al., "Differentiation-dependent Expression of I and Sialyl I Antigens in the Developing Lung of Human Embryos and in Lung Cancers," *Cancer Research* 50: 7603-7611, 1990.

Jeffrey et al., "Affinity Chromatography of Carbohydrate-Specific Immunoglobulins: Coupling of Oligosaccharides to Sepharose ," *Biochem. Biophys. Res. Commun.* 62:608-613, 1975.

Jentsch, K.D. et al., "Inhibition of Human Immunodeficiency Virus Type I Reverse Transcriptase by Suramin-related Compounds," *The Journal of General Virology* 68(8): 2183-2192, 1987.

Kannagi et al., "New Globoseries Glycosphingolipids in Human Teratocarcinoma Reactive with the Monoclonal Antibody Directed to a Developmentally Regulated Antigen, Stage-specific Embryonic Antigen 3," *J. Biol. Chem.* 258(14):8934-8942, 1983.

Kannagi et al., "Stage-specific embryonic antigens (SSEA-3 and -4) are epitopes of a unique globo-series ganglioside isolated from human teratocarcinoma cells," *Embo J.* 2(12):2355-2361, 1983.

Karaivanova et al., "Partial Characterization of Microsomal Sialyltransferase From Chicken Liver and Hepatoma Mc-29: II. Measurement of Enzyme Activities Utilizing Microsomal Glycoproteins as Exogenous Acceptors," *Cancer Biochem. Biophys.* 11:311-315, 1990.

Kitagawa et al., "Characterization of Mucin-Type Oligosaccharides With the Sialyl-$Le^a$ Structure From Human Colorectal Adenocarcinoma Cells," *Biochem. Biophys. Res. Commun.* 178(3):1429-1436, 1991.

Kitagawa et al., "Immunoaffinity Isolation of a Sialyl-$Le^a$ Oligosaccharide from Human Milk," *J. Biochem.* 104:591-594, 1988.

Köhler and Milstein, "Continuous cultures of fused cells secreting antibody of predefined specificity," *Nature* 256:495-497, 1975.

Köhler and Milstein, "Derivation of specific antibody-producing tissue culture and tumor lines by cell fusion," *Eur. J. Immunol.* 6:511-519, 1976.

Kojima and Hakomori, "Specific Interaction between Gangliotriaosylceramide ($G_{g3}$) and Sialosyllactosylceramide ($G_{M3}$) as a Basis for Specific Cellular Recognition between Lymphoma and Melanoma Cells," *J. Biol. Chem.* 264(34):20159-20162, 1989.

Koprowski et al., "Colorectal Carcinoma Antigens Detected by Hybridoma Antibodies," *Somatic Cell Genetics* 5(6):957-972, 1979.

Korgan, T.P. et al., "Novel Synthetic Inhibitors of Selectin-Mediated Cell Adhesion: Synthesis of 1,6-Bis[3-(3-carboxymethylphenyl)-r-(2-$\alpha$-D-monnopyranosyloxy)phenyl]hexane (TBC1269)," *J. Med. Chem* 41:1099-1111, 1998.

Korgan, T.P. et al., "Rational Design and Synthesis of Small Molecule, Non-oligosaccharide Selectin Inhibitors: ($\alpha$-D-Mannopyranosyloxy)biphenyl-Substituted Corboxylic Acids," *J. Med. Chem.* 38: 4976-4984, Dec. 22, 1995.

Kuzuoka, "Antitumor activity of murine monoclonal antibody NCC-ST-421," *Chem. Ab.* 115:27344v, 1991.

Lamblin et al., "Primary Structure Determination of Five Sialylated Oligosaccharides Derived from Bronchial Mucus Glycoproteins of Patients Suffering from Cystic Fibrosis. The Occurrence of the NeuAc$\alpha$(2$\rightarrow$3)Gal$\beta$(1$\rightarrow$4)[Fuc$\alpha$(1$\rightarrow$3)]GlcNAc$\beta$(1$\rightarrow\bullet$) Structural Element Revealed By 500-Mhz H NMR Spectroscopy," *Journal of Biological Chemistry* 259(14):9051-9058, 1984.

Larsen et al., PADGEM-Dependent Adhesion of Platelets to Monocytes and Neutrophils Is Mediated by a Lineage-Specific Carbohydrate, LNF III (CD15), *Cell* 63:467-474, 1990.

Lindenberg et al., "Carbohydrate binding properties of mouse embryos," *J. Reprod. Fert.* 89:431-439, 1990.

Lipartiti et al., "Monosialoganglioside GM1 Reduces NMDA Neurotoxicity in Neonatal Rat Brain," *Experimental Neurology* 113:301-305, 1991.

Lowe et al., "A transfected human fucosyltransferase cDNA determines biosynthesis of oligosaccharide ligand(s) for endothelial-leukocyte adhesion molecule I," *Biochem. Soc. Trans.* 19(3):649-653, 1991.

Lowe et al., "ELAM-1-Dependent Cell Adhesion to Vascular Endothelium Determined by a Transfected Human Fucosyltransferase cDNA," *Cell* 63: 475-484, 1990.

Macher et al., "A Novel Carbohydrate, Differentiation Antigen on Fucogangliosides of Human Myeloid Cells Recognized by Monoclonal Antibody VIM-2," *Journal of Biological Chemistry* 263:(21):10186-10191, 1988.

Magnani et al., "Identification of the Gastrointestinal and Pancreatic Cancer-associated Antigen Detected by Monoclonal Antibody 19-9 in the Sera of Patients as a Mucin," *Cancer Res.* 43:5489-5492, 1983.

Magnani et al., "A Monoclonal Antibody-defined Antigen Associated with Gastrointestinal Cancer Is a Ganglioside Containing Sialylated Lacto-$N$-fucopentaose II," *Journal of Biological Chemistry* 257(23):14365-14369, 1982.

Magnani, J., "Carbohydrate Sequences Detected By Murine Monoclonal Antibodies," *Chemistry and Physics of Lipids* 42:65-74, 1986.

Magnani, J., "Potent Glycomimetic Inhibitors of the Adhesion Molecule, PA-IIL, for the Bacterial Pathogen, *Pseudomonas auroginosa*," *Glycobiology* 13(11): 854, Abstract No. 104, Oct. 2003.

Mulligan and Berg, "Selection for animal cells that express the *Escherichia coli* gene coding for xanthine-gunine phosphoribosyltransferase," *Proc. Natl. Acad. Sci. USA* 78:2072-2076, 1981.

Nicolaou et al., "Total Synthesis of the Tumor-Associated Le$^X$ Family of Glycosphingolipids," *J. Amer. Chem. Soc.* 112:3693-3695, 1990.

Nudelman et al., "Novel Fucolipids of Human Adenocarcinoma: Disialosyl Le$^a$ Antigen (III$^4$FucIII$^6$NeuAcIV$^3$NeuAcLc$_4$) of Human Colonic Adenocarcinoma and the Monoclonal Antibody (FH7) Defining This Structure," *J. Biol. Chem.* 261:5487-5495, 1986.

Örhlein, R., "Carbohydrates and Derivatives as Potential Drug Candidates with Emphasis on the Selectin and Linear-B Area," *Mini Reviews in Medicinal Chemistry* 1: 349-361, 2001.

Palcic et al., "Enzymic Synthesis of Oligosaccharides Terminating in the Tumor-Associated Sialyl-Lewis-a Determinant," *Carbohydr. Res.* 190:1-11, 1989.

Palcic et al., "Regulation on $N$-Acetylglucosaminyltransferase V Activity. Kinetic Comparisons of Parental, Rous Sarcoma Virus-Transformed BHK, and L-Phytohemagglutinin-Resistant BHK Cells Using Synthetic Substrates and an Inhibitory Substrate Analog," *J. Biol. Chem.* 265:6759-6769, 1990.

Palcic et al., "A Bisubstrate Analog Inhibitor for $\alpha(1\rightarrow2)$-Fucosyltransferase," *J. Biol. Chem.* 264:17174-17181, 1989.

Palma-Vargas, J.M. et al., "Small-Molecule Selectin Inhibitor Protects Against Liver Inflammatory Response After Ischemia and Reperfusion," *J. Am. Coll. Surg.* 185: 365-372, 1997.

Phillips et al., "ELAM-1 Mediates Cell Adhesion by Recognition of a Carbohydrate Ligand, Sialyl-Le$^X$," *Science* 250:1130-1132, 1990.

Picker et al., "The Neutrophil Selectin LECAM-1 Presents Carbohydrate Ligands to the Vascular Selectins ELAM-1 and GMP-140," *Cell* 66:921-933, 1991.

Prokazova et al., "Sialylated lactosylceramides. Possible inducers of non-specific immunosuppression and atherosclerotic lesions," *European Journal of Biochemistry* 172:1-6, 1988.

Rauvala et al., "Studies on Cell Adhesion and Recognition. I. Extent and Specificity of Cell Adhesion Triggered by Carbohydrate-reactive Proteins (Glycosidases and Lectins) and by Fibronectin," *J. Cell Biol.* 88:127-137, 1981.

Rice and Bevilacqua, "An Inducible Endothelial Cell Surface Glycoprotein Mediates Melanoma Adhesion," *Science* 246:1303-1306, 1989.

Ruoslahti and Pierschbacher, "New Perspectives in Cell Adhesion: RGD and Integrins," *Science* 238:491-497, 1987.

Sakurai et al., "Selection of a Monoclonal Antibody Reactive with a High-Molecular-Weight Glycoprotein Circulating in the Body Fluid of Gastrointestinal Cancer Patients," *Cancer Research* 48:4053-4058, 1988.

Sastry et al., "Cloning of the immunological repertoire in *Escherichia coli* for generation of monoclonal catalytic antibodies: Construction of a heavy chain variable region-specific cDNA library," *Proc. Natl. Acad. Sci. USA* 86:5728-5732, 1989.

Scharfman, A. et al., "*Pseudomonas aeruginosa* binds to neoglycoconjugates bearing mucin carbohydrate determinants and predominantly to sialyl-Lewis x conjugates," *Glycobiology* 9(8): 757-764, 1999.

Scharfman, A. et al., "Recognition of Lewis x Derivatives Present on Mucins by Flagellar Components of *Pseudomonas aeruginosa*," *Infection and Immunity* 69(9): 5243-5248, Sep. 2001.

Shitara et al., "Application of Anti-Sialyl Le$_a$ Monoclonal antibody, KM231, for Immunotherapy of Cancer," *Anticancer Res.* 11:2003-2014, 1991.

Siuzdak et al., "Examination of the Sialyl Lewis X—Calcium Complex By Electrospray Mass Spectrometry," *Bioorganic & Medicinal Chemistry Letters* 4(24): 2863-2866, 1994.

Sprengard, U. et al., "Synthesis and Biological Activity of Novel Sialyl-Lewis$^X$ Conjugates," *Bioorganic & Medicinal Chemistry Letters* 6(5): 509-514, 1996.

Stanley and Atkinson, "The LEC11 Chinese Hamster Ovary Mutant Synthesizes $N$-Linked Carbohydrates Containing Sialylated, Fucosylated Lactosamine Units. Analysis By One-and Two-Dimensional H NMR Spectroscopy," *J. Biol. Chem.* 263(23):11374-11381, 1988.

Stephens and Cockett, "The construction of highly efficient and versatile set of mammalian expression vectors," *Nucleic Acids Research.* 17:7110, 1989.

Streeter et al., "Immunohistologic and Functional Characterization of a Vascular Addressin Involved in Lymphocyte Homing into Peripheral Lymph Nodes," *Journal of Cell Biology* 107: 1853-1862, 1988.

Stroud et al., "Extended Type 1 Chain Glycosphingolipids: Dimeric Le$^a$ (III$^4$V$^4$Fuc$_2$Lc$_6$) as Human Tumor-associated Antigen," *J. Biol. Chem.* 266(13):8439-8446, 1991.

Svenson and Lindberg, "Coupling of Acid Labile Salmonella Specific Oligosaccharides to Macromolecular Carriers," *J. Immunol. Meth.* 25:323-335, 1979.

Takada et al., "Adhesion of Human Cancer Cells to Vascular Endothelium Mediated by a Carbohydrate Antigen, Sialyl Lewis A$^1$," *Biochem. Biophys. Res. Commun.* 179(2):713-719, 1991.

Takeichi, M., "Cadherins: a molecular family essential for selective cell-cell adhesion and animal morphogenesis," *Trends Genet.* 3(8):213-217, 1987.

Thoma, G. et al., "A readily Available, Highly Potent E-Selectin Antagonist," *Angew. Chem. Int. Ed.* 40(19): 3644-3647, 2001.

Thoma, G. et al., "Preorganization of the Bioactive Conformation of Sialyl Lewis$^X$ Analogues Correlates with Their Affinity to E-Selectin," *Angew. Chem. Int. Ed.* 40(10): 1941-1945, 2001.

Thoma, G. et al., "Synthesis and Biological Evaluation of a Sialyl Lewis X Mimic with Significantly Improved E-selectin Inhibition," *Bioorganic & Medicinal Chemistry Letters* 11: 923-925, 2001.

Tilton, R.G., "Endotoxin-Induced Leukocyte Accumulation in Aqueous Fluid of Rats is Decreased by a Small Molecule Selectin," *Investigative Opthalmology & Visual Science* 37(3): S918, Abstract No. 4227, Feb. 15, 1996.

Trouet et al., "A covalent linkage between daunorubicin and proteins that is stable in serum and reversible by lysosomal hydrolases, as required for a lysosomotropic drug-carrier conjugate: In vitro and in vivo studies," *Proc. Natl. Acad. Sci. USA* 79:626-629, 1982.

Tyrrell et al., "Structural requirements for the carbohydrate ligand of E-selectin," *Proc. Natl. Acad. Sci. USA* 88:10372-10376, 1991.

Waldmann, H. et al., "Synthesis of 2-Acetamindo-2-Deoxyglucosylasparagine Glyco-Tripeptide and -Pentapeptides By Selective C- and N-Terminal Elongation of the Peptide Chain," *Carbohydrate Research 196*: 75-93, 1990.

Walz et al., "Recognition by ELAM-1 of the Sialyl-Le$^X$ Determinant on Myeloid and Tumor Cells," *Science 250*:1132-1135, 1990.

Ward and Mulligan, "Blocking of adhesion molecules in vivo as anti-inflammatory therapy," *Immunology I*: 165-171, 1994.

Whisler and Yates, "Regulation of Lymphocyte Responses By Human Gangliosides. I. Characteristics of Inhibitory Effects and the Induction of Impaired Activation," *Journal of Immunology 125*(5):2106-2111, 1980.

Yamazaki, F. et al., "Syntheisis of an appropriately protected core glycotetraoside, a key intermediate for the synthesis of 'bisected' complex-type glycans of a glycoprotein," *Carbohydrate Research 201*: 15-30, 1990.

Zhou et al., "The Selectin GMP-140 Binds to Sialylated, Fucosylated Lactosaminoglycans on Both Myeloid and Nonmyeloid Cells," *Journal of Cell Biology 115*(2):557-564, 1991.

Zopf et al., "Affinity Purification of Antibodies Using Oligosaccharide-Phenethylamine Derivatives Coupled to Sepharose," *Meth. Enzymol. 50*:171-175, 1978.

* cited by examiner

Structures for Lectin assays

Compound A

Compound B

Glycomimetic 1

| Compound | IC$_{50}$(μM) |
|---|---|
| Galactose | 277 |
| Melibiose | 111 |
| Glycomim. 1 | 47 |

Glycomimetic 1 fucose is inactive

Glycomimetic 1

Galactose is inactive

GLYCOMIMETRIC INHIBITORS OF THE PA-IL LECTIN, PA-IIL LECTIN OR BOTH THE LECTINS FROM *PSEUDOMONAS*

CROSS-REFERENCES TO RELATED APPLICATIONS

This application claims the benefit under 35 U.S.C. § 119 (e) of U.S. Provisional Patent Application No. 60/706,546 filed Aug. 9, 2005 and U.S. Provisional Application No. 60/810,190 filed Jun. 1, 2006; which applications are incorporated herein by reference in their entirety.

BACKGROUND OF THE INVENTION

1. Field of the Invention

The present invention relates generally to compounds, compositions and methods for the diagnosis and therapy of diseases in warm-blooded animals (e.g., in humans) involving infections with and colonization by *Pseudomonas* bacteria, including *Pseudomonas aeruginosa* in the lungs of patients with cystic fibrosis. The invention relates more particularly to the use of one or more compounds selective for binding PA-IL and/or PA-IIL lectins of *Pseudomonas* bacteria. These compounds are useful for diagnosis and/or therapeutic intervention of the colonization of *Pseudomonas* bacteria, or may be linked to an agent(s) to target and effectively arrest or kill *Pseudomonas* bacteria.

2. Description of the Related Art

*Pseudomonas* infections occur in a variety of medical conditions and can be life threatening. *Pseudomonas* is an opportunistic bacterium. Examples of individuals at risk include cystic fibrosis patients, burn patients, and patients on ventilators. Cystic fibrosis is described below as a representative example of a medical condition which can involve infection with *Pseudomonas* bacteria.

Cystic Fibrosis (CF) is the most common lethal genetic disease among the Caucasian population. CF is caused by mutations in the gene encoding the cystic fibrosis transmembrane conductance regulator (CFTR), which acts as a chloride channel. The genetic mutations of CFTR which alter ion movements also affect the N-glycosylation of CFTR as well as other cell surface molecules. All of the exocrine glands of the patients are affected; however, the lungs are the primary site of morbidity and mortality. The general change in glycosylation is associated with an increase in infectivity by *Pseudomonas aeruginosa*. The salivary and respiratory mucins from CF patients also contain altered glycosylation patterns.

The major cause of morbidity and mortality in CF patients is chronic lung colonization by the bacterium, *Pseudomonas aeruginosa*, which results in pronounced lung infection with a robust neutrophilic inflammatory response leading to destruction of the lungs and death. Colonization by *P. aeruginosa* initiates during the sessile phase of the bacteria in which virulence factors are secreted in concert. Two virulence factors that bind carbohydrates are lectins. These lectins, known as PA-IL and PA-IIL, bind these oligosaccharide structures with high affinity and represent a potential molecular target to block bacterial colonization. Patients that are never fully colonized by the bacteria maintain an excellent long-term prognosis. Due to the difficulties in the current approaches in the art for prevention of colonization in an individual by *Pseudomonas* bacteria, there is a need for improved compounds, compositions and methods.

BRIEF SUMMARY OF THE INVENTION

Briefly stated, this invention provides compounds, compositions and methods for utilizing both the PA-IIL and PA-IL lectins, or either one alone, expressed by *Pseudomonas* bacteria for the detection of *Pseudomonas* bacteria and the diagnosis and therapy of disease involving *Pseudomonas* bacteria, including human disease. For example, compounds of the present invention that have high affinity binding to the PA-IIL lectin, the PA-IL lectin or both lectins from *P. aeruginosa* will have a beneficial therapeutic effect on CF patients. Furthermore, these compounds may be administered in combination therapy with antibiotics or may be conjugated, for example, with antibiotics to increase the efficacy and lower the dose, thereby avoiding well known deleterious side effects of many antibiotics. Given that these binding sites are crucial for the colonization and pathogenicity of the bacterium, mutations in this target to become resistant to this conjugate therapy should result in non-pathogenic forms of the bacteria.

One embodiment of the present invention provides a compound or physiologically acceptable salt thereof, having the formula:

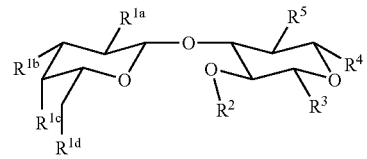

wherein:
where —O— separating the two rings in the formula is in an alpha or beta 1-3 linkage;
$R^1$=independently selected from OH, NHAc, 6' sulfated GlcNAc, 6' carboxylated GlcNAc, GalNAc, galactose linked by an O glycosidic bond, a C glycosidic bond or an S glycosidic bond, thiodigalactoside, 6' sulfated galactose and 6' carboxylated galactose, with the proviso that three of the four $R^1$ are independently selected from OH and NHAc and one $R^1$ is not OH or NHAc;
$R^2$=H, a fucose, a galactose, an arabinose, a fructose, a mannose, cyclohexane, substituted cyclohexane, tetrahydropyran, substituted tetrahydropyran, piperidine, substituted piperidine, a polyol or substituted polyol;
$R^3$=$(CH_2)_p$, $NH_2$, —$CH_2$—OH, —$CH_2$—(NH)$_q$X or

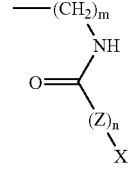

where m, n and q are independently selected from 0-1, p is 1-20, Z is N, O or S, and X is NH—$C_1$-$C_8$ alkyl, $C_3$-$C_8$ cycloalkyl, substituted $C_3$-$C_8$ cycloalkyl, $C_1$-$C_8$ alkyl, $C_6$-$C_{14}$ aryl, substituted $C_6$-$C_{14}$ aryl, $C_1$-$C_{14}$ heteroaryl, substituted $C_1$-$C_{14}$ heteroaryl, non-aryl $C_1$-$C_{14}$ heterocycle or substituted non-aryl $C_1$-$C_{14}$ heterocycle, NHCH$_2$Ph, N(CH$_2$Ph)$_2$, NHSO$_3$Na, NHCO—$C_6H_4$—COOH (ortho), NHCOPh, NHCO—C$_6$H$_4$—Cl (para), NHCO—C$_6$H$_4$—OMe (para), NHCO—C$_6$H$_4$—NO$_2$ (para), NHCO—C$_6$H$_4$-Ph (para), NHCO—C$_6$H$_3$(OMe)$_2$ (meta, para), NHCO(2-naphthyl), NHCO—C$_6$H$_4$—OCH$_2$Ph (para), N(CH$_2$Ph)COPh, NHCOCH$_2$CH$_2$Ph, NHCOCHPh$_2$, NHCOMe, NHCO(cyclo-C$_6$H$_{11}$), NHSO$_2$—C$_6$H$_4$—Me (para), NHCONHEt, NHCONHPh, NHCOOCH$_2$—C$_6$H$_4$—NO$_2$ (para), NHCOOCH$_2$(2-naphthyl), or NHCOOCH$_2$Ph;

R$^4$=H, NHAc, —O-Lactose, substituted —O-Lactose, —O-Lactosamine, substituted —O-Lactosamine, NHAc substituted with N-glycolyl, polyethylene glycol or substituted polyethylene glycol; and R$^5$=H, NHAc, or NHAc substituted with N-glycolyl.

A compound or salt thereof of the present invention may be in combination with a pharmaceutically acceptable carrier or diluent.

In another embodiment, the present invention provides a conjugate comprising a therapeutic agent linked to a compound as set forth above.

Another embodiment of the present invention provides a method of inhibiting *Pseudomonas* bacteria infection in a warm-blooded animal comprising administering to the animal in an amount effective to inhibit one or more lectins of the bacteria a compound comprising a compound or physiologically acceptable salt thereof, having the formula:

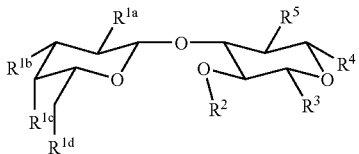

wherein:
where —O— separating the two rings in the formula is in an alpha or beta 1-3 linkage;

R$^1$=independently selected from OH, NHAc, 6' sulfated GlcNAc, 6' carboxylated GlcNAc, GalNAc, galactose linked by an O glycosidic bond, a C glycosidic bond or an S glycosidic bond, thiodigalactoside, 6' sulfated galactose and 6' carboxylated galactose, with the proviso that three of the four R$^1$ are independently selected from OH and NHAc and one R$^1$ is not OH or NHAc;

R$^2$=H, a fucose, a galactose, an arabinose, a fructose, a mannose, cyclohexane, substituted cyclohexane, tetrahydropyran, substituted tetrahydropyran, piperidine, substituted piperidine, a polyol or substituted polyol;

R$^3$=(CH$_2$)$_p$, NH$_2$, —CH$_2$—OH, —CH$_2$—(NH)$_q$X or

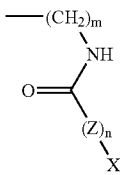

where m, n and q are independently selected from 0-1, p is 1-20, Z is N, O or S, and X is NH—C$_1$-C$_8$ alkyl, C$_3$-C$_8$ cycloalkyl, substituted C$_3$-C$_8$ cycloalkyl, C$_1$-C$_8$ alkyl, C$_6$-C$_{14}$ aryl, substituted C$_6$-C$_{14}$ aryl, C$_1$-C$_{14}$ heteroaryl, substituted C$_1$-C$_{14}$ heteroaryl, non-aryl C$_1$-C$_{14}$ heterocycle or substituted non-aryl C$_1$-C$_{14}$ heterocycle, NHCH$_2$Ph, N(CH$_2$Ph)$_2$, NHSO$_3$Na, NHCO—C$_6$H$_4$—COOH (ortho), NHCOPh, NHCO—C$_6$H$_4$—Cl (para), NHCO—C$_6$H$_4$—OMe (para), NHCO—C$_6$H$_4$—NO$_2$ (para), NHCO—C$_6$H$_4$-Ph (para), NHCO—C$_6$H$_3$(OMe)$_2$ (meta, para), NHCO(2-naphthyl), NHCO—C$_6$H$_4$—OCH$_2$Ph (para), N(CH$_2$Ph)COPh, NHCOCH$_2$CH$_2$Ph, NHCOCHPh$_2$, NHCOMe, NHCO(cyclo-C$_6$H$_{11}$), NHSO$_2$—C$_6$H$_4$—Me (para), NHCONHEt, NHCONHPh, NHCOOCH$_2$—C$_6$H$_4$—NO$_2$ (para), NHCOOCH$_2$(2-naphthyl), or NHCOOCH$_2$Ph;

R$^4$=H, NHAc, —O-Lactose, substituted —O-Lactose, —O-Lactosamine, substituted —O-Lactosamine, NHAc substituted with N-glycolyl, polyethylene glycol or substituted polyethylene glycol; and R$^5$=H, NHAc, or NHAc substituted with N-glycolyl.

In another embodiment, the present invention provides a method of detecting *Pseudomonas* bacteria comprising contacting a sample with a diagnostic agent linked to a compound comprising a compound as set forth above, under conditions sufficient for the compound to bind to the bacteria or its lectin products if present in the sample; and detecting the agent present in the sample, wherein the presence of agent in the sample is indicative of the presence of *Pseudomonas* bacteria.

In another embodiment, the present invention provides a method of immobilizing *Pseudomonas* bacteria on a solid support comprising contacting, under conditions sufficient for binding, a sample containing *Pseudomonas* bacteria with a compound comprising a compound as set forth above that is immobilized on a solid support; and separating the sample from the solid support.

In other embodiments, the compounds and conjugates described herein may be used in the preparation of a medicament for the inhibition of *Pseudomonas* bacteria.

These and other aspects of the present invention will become apparent upon reference to the following detailed description and attached drawings. All references disclosed herein are hereby incorporated by reference in their entirety as if each was incorporated individually.

DETAILED DESCRIPTION OF THE INVENTION

Figure 1:
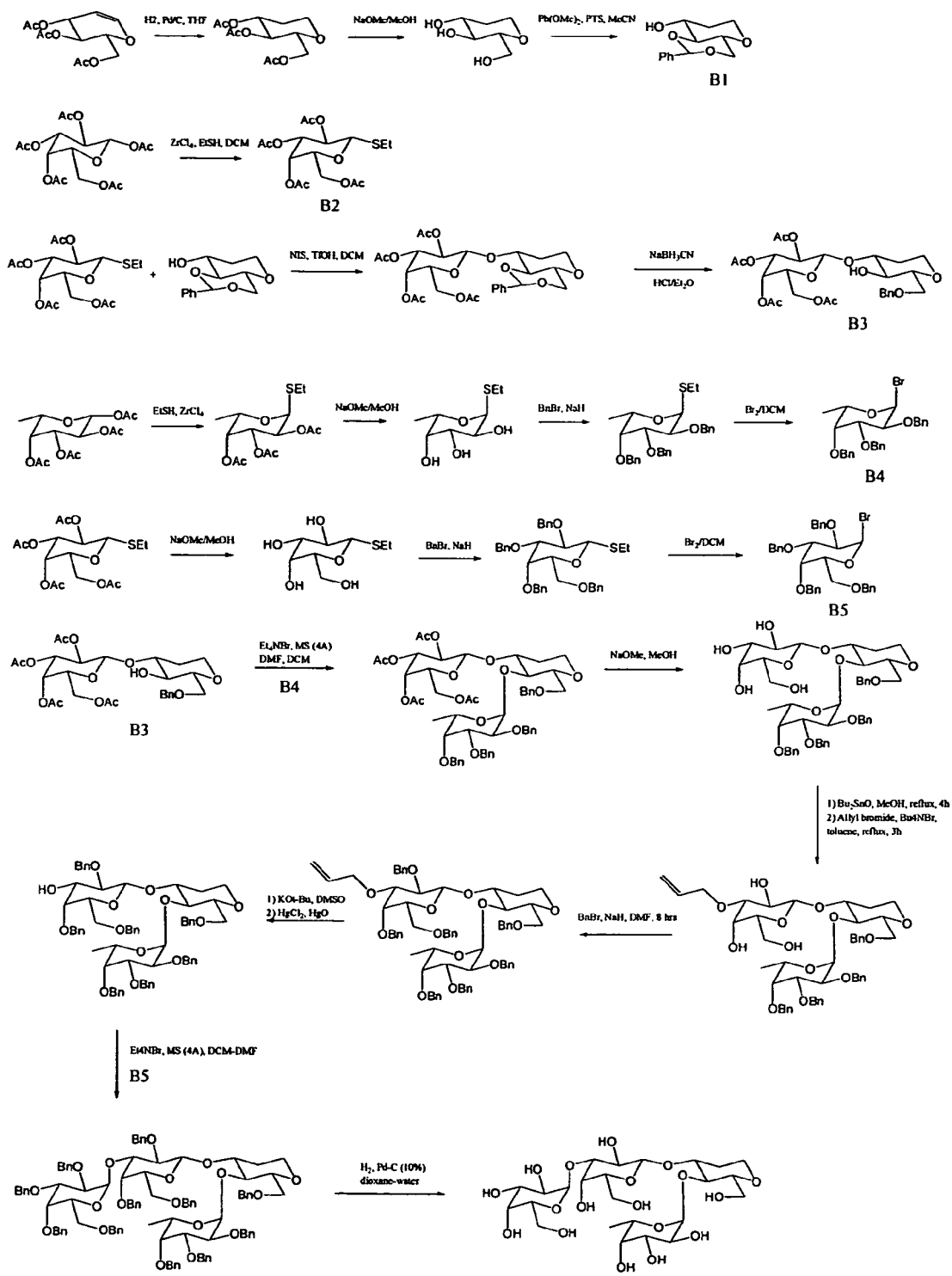
FIG. 1 is a diagram illustrating the synthesis of a glycomimetic compound.
Figure 2A:
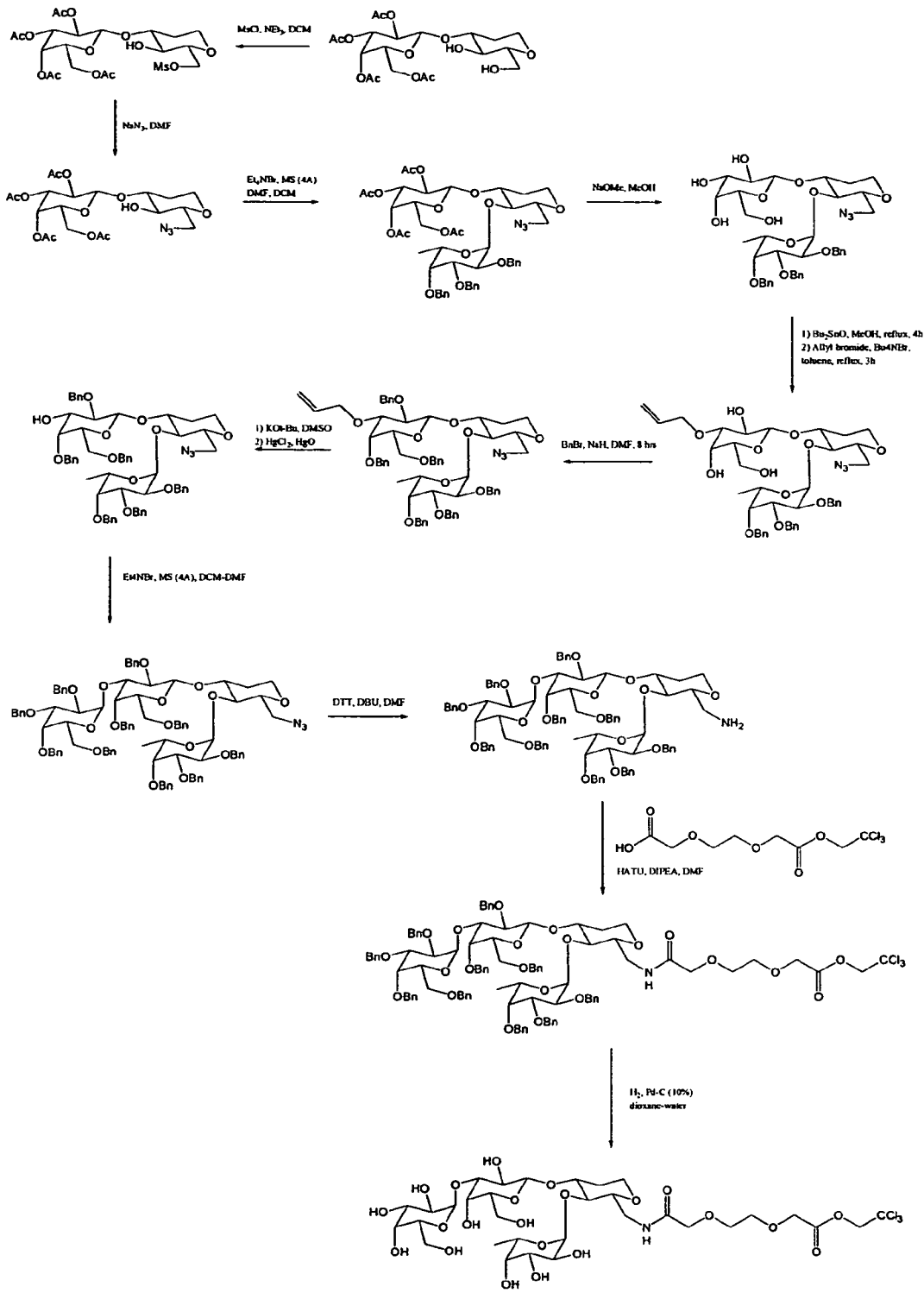
FIG. 2A is a diagram illustrating the synthesis of a glycomimetic compound containing a linker arm.
Figure 2B:
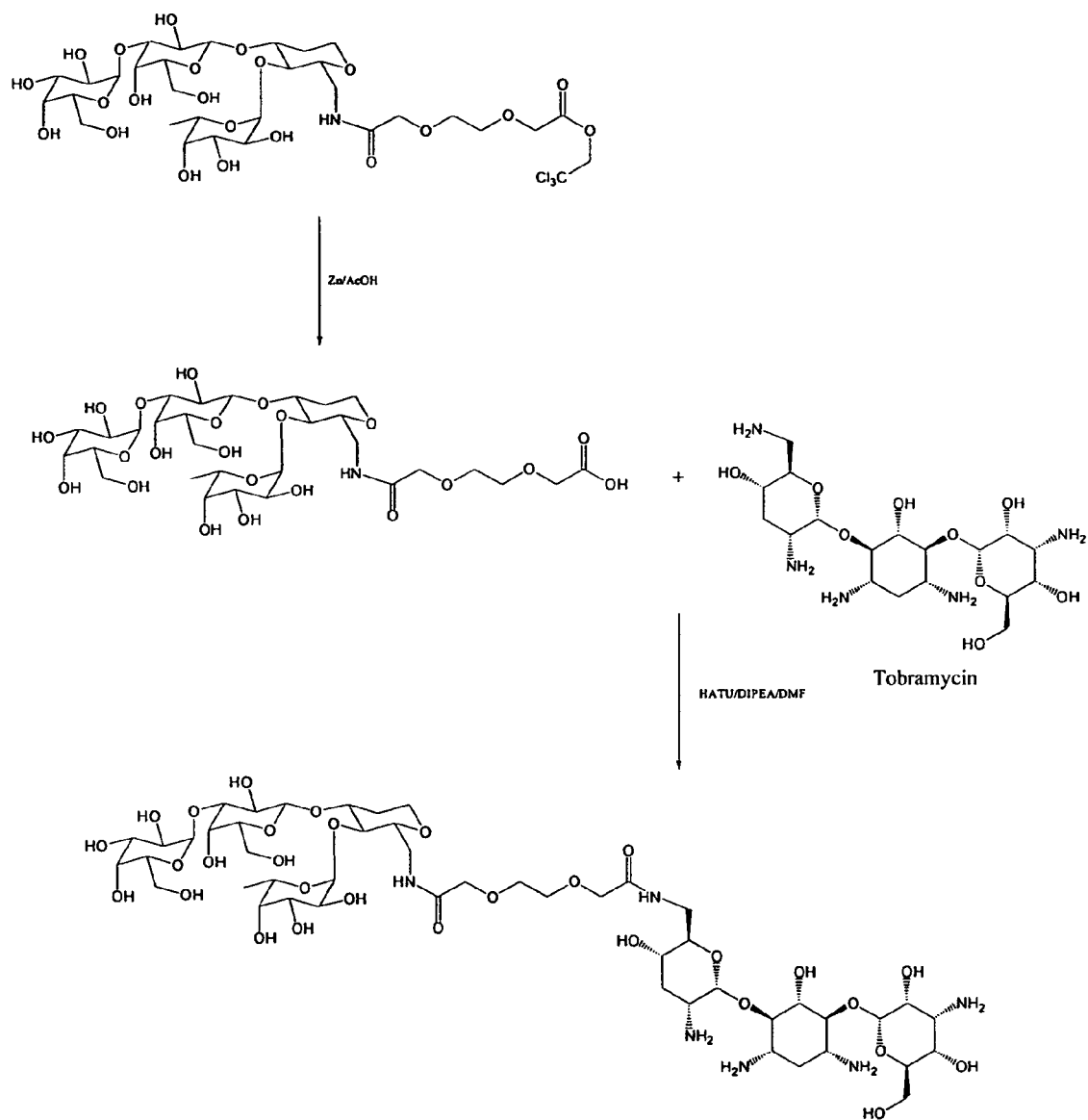
FIG. 2B is a diagram illustrating the conjugation of the compound of FIG. 2A to the antibiotic tobramycin.

As noted above, the present invention provides compounds and compositions that bind *Pseudomonas* bacterial lectins (e.g., *P. aeruginosa* lectins) and may be used in the diagnosis and therapy of disease.

Glycomimetic Compounds

The term "Glycomimetic compound," as used herein, refers to a compound (including physiologically acceptable salts thereof) that has high affinity for the PA-IL lectin, PA-IIL lectin or both lectins from *Pseudomonas* bacteria. Embodiments of the structures of the Glycomimetic compounds of this invention have the formula:

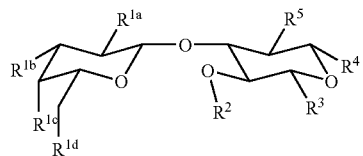

wherein:
where —O— separating the two rings in the formula is in an alpha or beta 1-3 linkage;
$R^1$=independently selected from OH, NHAc, 6' sulfated GlcNAc, 6' carboxylated GlcNAc, GalNAc, galactose linked by an O glycosidic bond, a C glycosidic bond or an S glycosidic bond, thiodigalactoside, 6' sulfated galactose and 6' carboxylated galactose;
$R^2$=H, a fucose, a galactose, an arabinose, a fructose, a mannose, cyclohexane, substituted cyclohexane, tetrahydropyran, substituted tetrahydropyran, piperidine, substituted piperidine, a polyol or substituted polyol;
$R^3$=$(CH_2)_p$, $NH_2$, $CH_2$—OH, —$CH_2$—$(NH)_q$X or

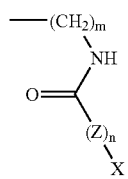

where m, n and q are independently selected from 0-1, p is 1-20, Z is N, O or S, and X is NH—$C_1$-$C_8$ alkyl, $C_3$-$C_8$ cycloalkyl, substituted $C_3$-$C_8$ cycloalkyl, $C_1$-$C_8$ alkyl, $C_6$-$C_{14}$ aryl, substituted $C_6$-$C_{14}$ aryl, $C_1$-$C_{14}$ heteroaryl, substituted $C_1$-$C_{14}$ heteroaryl, non-aryl $C_1$-$C_{14}$ heterocycle or substituted non-aryl $C_1$-$C_{14}$ heterocycle, $NHCH_2Ph$, $N(CH_2Ph)_2$, $NHSO_3Na$, NHCO—$C_6H_4$—COOH (ortho), NHCOPh, NHCO—$C_6H_4$—Cl (para), NHCO—$C_6H_4$—OMe (para), NHCO—$C_6H_4$—$NO_2$ (para), NHCO—$C_6H_4$-Ph (para), NHCO—$C_6H_3(OMe)_2$ (meta, para), NHCO(2-naphthyl), NHCO—$C_6H_4$—$OCH_2Ph$ (para), $N(CH_2Ph)COPh$, $NHCOCH_2CH_2Ph$, $NHCOCHPh_2$, NHCOMe, NHCO(cyclo-$C_6H_{11}$), $NHSO_2$—$C_6H_4$—Me (para), NHCONHEt, NHCONHPh, NHCOOCH$_2$—$C_6H_4$—$NO_2$ (para), $NHCOOCH_2$(2-naphthyl), or $NHCOOCH_2Ph$;
$R^4$=H, NHAc, —O-Lactose, substituted —O-Lactose, —O-Lactosamine, substituted —O-Lactosamine, NHAc substituted with N-glycolyl, polyethylene glycol or substituted polyethylene glycol; and
$R^5$=H, NHAc, or NHAc substituted with N-glycolyl.

All compounds (or conjugates thereof) useful in the present invention include physiologically acceptable salts thereof.

Glycomimetic compounds of the present invention include the formula set forth above with substituents $R^1$-$R^5$. Where a substituent option (i.e., atom or group) for $R^1$-$R^5$ possesses a "-" this is to indicate the point of attachment (to a ring for $R^{1a}$, $R^{1b}$, $R^{1c}$ and $R^3$-$R^5$, to $CH_2$ for $R^{1d}$, and to O for $R^2$), and does not represent $CH_2$ or $CH_3$. In the above formula, there is an oxygen (—O—) linking the two rings depicted in the formula. The oxygen may be in an alpha 1-3 linkage or a beta 1-3 linkage.

As used herein, a line to which no group is depicted represents the bond that attaches the substituent to the structure depicted by the general formula. As used herein, a "$C_6$-$C_{14}$ aryl" refers to an aromatic substituent with six to fourteen carbon atoms in one or multiple rings which may be separated by a bond or an alkyl group or be fused. As used herein, a "$C_1$-$C_{14}$ heteroaryl" is similar to a "$C_6$-$C_{14}$ aryl," except the aromatic substituent possesses at least one heteroatom (such as N, O or S) in place of a ring carbon. Examples of aryls and heteroaryls include phenyl, naphthyl, diphenyl, pyridinyl and pyrimidinyl.

$R^1$ is composed of $R^{1a}$, $R^{1b}$, $R^{1c}$ and $R^{1d}$, as depicted in the above formula. $R^{1a}$ is attached at carbon position 2. $R^{1b}$ is attached at carbon position 3, $R^{1c}$ is attached at carbon position 4. $R^{1d}$ is attached at carbon position 6, which in turn is attached at carbon position 5.

Examples of $R^1$ substituents include GalNAc, 6' sulfated GlcNAc and 6' carboxylated GlcNAc. The abbreviation "GlcNAc" represents N-Acetylglucosamine and "GalNAc" represents N-Acetylgalactosamine. Other $R^1$ substituents are OH, NHAc, galactose, thiodigalactoside, 6' sulfated galactose and 6' carboxylated galactose. Galactose is linked by an O glycosidic bond, a C glycosidic bond or an S glycosidic bond. Where $R^1$ as set forth with the above formula is galactose, 6' sulfated galactose or 6' carboxylated galactose, $R^1$ in an embodiment is attached by an alpha 1-3 linkage, but the linkage may be beta. In embodiments, only one of the four $R^1$ is other than OH or NHAc (i.e., selected from one of the $R^1$ substituents listed other than OH or NHAc).

Examples of $R^2$ substituents include monosaccharides, such as fucose, galactose, arabinose, fructose or mannose. The monosaccharides possess a D- and an L-form. Such monosaccharides include L-fucose, L-galactose, D-arabinose, D-fructose and D-mannose. A monosaccharide of $R^2$ may be replaced with a mimic of the monosaccharide. For example, a monosaccharide ring may be replaced with a cyclohexane, substituted cyclohexane, tetrahydropyran, substituted tetrahydropyran, piperidine, substituted piperidine, a polyol or substituted polyol. Alternatively, or in addition to the replacement of a ring, substituents may be added to a ring as replacement for, or in addition to, existing substituents or both. For example, one or more hydroxyl groups may be replaced with alkoxy groups (such as methoxy, ethoxy, propoxy, etc.), halides (such as fluorine, chlorine, etc.), esters and amides. Similarly, for example, one or more hydrogens of cyclohexane, tetrahydropyran or piperidine may be replaced with such groups (alkoxy, halide, ester and amide) to produce a substituted cyclohexane, substituted tetrahydropyran or substituted piperidine, respectively.

Examples of $R^3$ substituents include $(CH_2)_p$ where p is 1-20, —$CH_2$—OH, $NH_2$, —$CH_2$—$(NH)_q$—X and —$(CH_2)_m$—NH—C(=O)—$(Z)_n$—X where m, n and q are independently selected from 0 and 1, and where X is NH—$C_1$-$C_8$ alkyl, $C_3$-$C_8$ cycloalkyl, substituted $C_3$-$C_8$ cycloalkyl, $C_1$-$C_8$ alkyl, $C_6$-$C_{14}$ aryl, substituted $C_6$-$C_{14}$ aryl, $C_1$-$C_{14}$ heteroaryl, substituted $C_1$-$C_{14}$ heteroaryl, non-aryl $C_1$-$C_{14}$ heterocycle or substituted non-aryl $C_1$-$C_{14}$ heterocycle. As used herein, "$C_1$-$C_8$ alkyl" refers to a saturated hydrocarbon which may be straight chained or branched. Examples are methyl, ethyl, propyl, isopropyl, butyl, isobutyl, and t-butyl. "$C_6$-$C_{14}$ aryl" and "$C_1$-$C_{14}$ heteroaryl" are as defined above. Examples are provided above. A "substituted $C_6$-$C_{14}$ aryl" is a $C_6$-$C_{14}$ aryl wherein at least one ring hydrogen is replaced with one or more atoms other than hydrogen. A "substituted $C_1$-$C_{14}$ heteroaryl" is a $C_1$-$C_{14}$ heteroaryl wherein at least one ring hydrogen or hydrogen attached to a heteroatom is replaced with one or more atoms other than hydrogen. Such atoms include carbon, oxygen, nitrogen, sulfur and halogen. A "non-aryl $C_1$-$C_{14}$ heterocycle" refers to a non-aromatic substituent with one to fourteen carbon atoms (with at least one heteroatom) in one or multiple rings which may be separated by a bond or fused. The third atom of a three member ring may be provided by the carbon to which $R^3$ is attached. Examples include piperidine, piperazine, pyrrolidine, and their oxygen and sulfur equivalents. A "substituted non-aryl $C_1$-$C_{14}$ heterocycle" is a non-aryl $C_1$-$C_{14}$ heterocycle wherein at least one ring hydrogen or hydrogen attached to a heteroatom is replaced with one or more atoms other than hydrogen. Such atoms include carbon, oxygen, nitrogen, sulfur and halogen. Examples of $R^3$ include NHCOPh, NHCO—$C_6H_4$—Cl (para), NHCO—$C_6H_4$—OMe (para), NHCO—$C_6H_4$—$NO_2$ (para), NHCO—$C_6H_4$-Ph (para), NHCO—$C_6H_3(OMe)_2$ (meta, para), NHCO(2-naphthyl), NHCO—$C_6H_4$—$OCH_2$Ph (para), N($CH_2$Ph)COPh, NHCOCH$_2$CH$_2$Ph, NHCOCHPh$_2$, NHCOMe, NHCO(cyclo-$C_6H_{11}$), NHSO$_2$—$C_6H_4$—Me (para), NHCONHEt, NHCONHPh, NHCOOCH$_2$—$C_6H_4$—$NO_2$ (para), NHCOOCH$_2$(2-naphthyl), or NHCOOCH$_2$Ph. The abbreviation "Ph" represents "phenyl".

Examples of $R^4$ substituents include H, NHAc, and NHAc substituted with N-glycolyl. It also includes —O-Lactose, substituted —O-Lactose, —O-Lactosamine, substituted —O-Lactosamine, polyethylene glycol and substituted polyethylene glycol.

Examples of $R^5$ substituents include H, NHAc, and NHAc substituted with N-glycolyl.

Examples of non-monosaccharide, ringed substituents include:

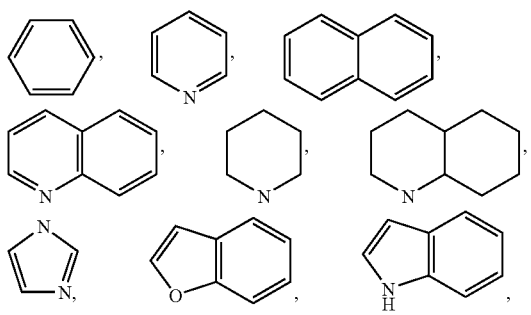

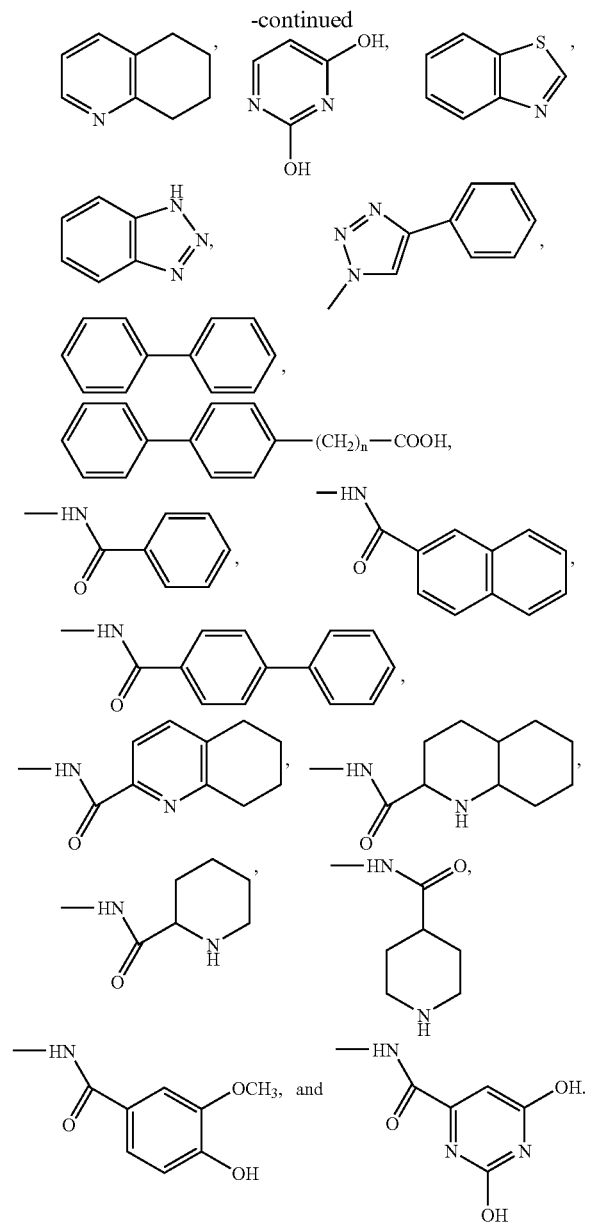

where n = 0-10,

For certain embodiments, it may be beneficial to also, or alternatively, link a diagnostic or therapeutic agent, such as a drug to a Glycomimetic compound, to form a conjugate where the linkage is covalent. As used herein, the term "therapeutic agent" refers to any bioactive agent intended for administration to a warm-blooded animal (e.g., a mammal such as a human) to prevent or treat a disease or other undesirable condition or to enhance the success of therapies. Therapeutic agents include antibiotics, hormones, growth factors, proteins, peptides, genes, non-viral vectors and other compounds.

Glycomimetic Compound Formulations

Glycomimetic compounds as described herein may be present within a pharmaceutical composition. A pharmaceutical composition comprises one or more Glycomimetic compounds in combination with one or more pharmaceutically or physiologically acceptable carriers, diluents or excipients. Such compositions may comprise buffers (e.g., neutral buffered saline or phosphate buffered saline), carbohydrates (e.g., glucose, mannose, sucrose or dextrans), mannitol, proteins, polypeptides or amino acids such as glycine, antioxidants, chelating agents such as EDTA or glutathione, adjuvants (e.g., aluminum hydroxide) and/or preservatives. Within yet other embodiments, compositions of the present invention may be formulated as a lyophilizate. Compositions of the present invention may be formulated for any appropriate manner of administration, including for example, aerosol, topical, oral, nasal, intravenous, intracranial, intraperitoneal, subcutaneous, or intramuscular administration.

A pharmaceutical composition may also, or alternatively, contain one or more active agents, such as drugs (e.g., antibiotics), which may be linked to a Glycomimetic compound or may be free within the composition. The attachment of an agent to a Glycomimetic compound may be covalent or non-covalent. An example of an active agent is tobramycin. Tobramycin alone has typically been administered intravenously or by inhalation.

The compositions described herein may be administered as part of a sustained release formulation (i.e., a formulation such as a capsule or sponge that effects a slow release of modulating agent following administration). Such formulations may generally be prepared using well known technology and administered by, for example, oral, rectal or subcutaneous implantation, or by implantation at the desired target site. Carriers for use within such formulations are biocompatible, and may also be biodegradable; preferably the formulation provides a relatively constant level of modulating agent release. The amount of Glycomimetic compound contained within a sustained release formulation depends upon the site of implantation, the rate and expected duration of release and the nature of the condition to be treated or prevented.

Glycomimetic compounds are generally present within a pharmaceutical composition in a therapeutically effective amount. A therapeutically effective amount is an amount that results in a discernible patient benefit, such as a measured or observed response of a condition associated with *Pseudomonas* infection.

Glycomimetic Compounds Methods of Use

In general, Glycomimetic compounds described herein may be used for achieving diagnostic and/or therapeutic results in disease (e.g., human disease) involving infection by *Pseudomonas* (e.g., *P. aeruginosa*) bacteria. Such diagnostic and/or therapeutic results may be achieved in vitro and/or in vivo in an animal, preferably in a mammal such as a human, provided that *Pseudomonas* (e.g., *P. aeruginosa*) or its products are ultimately contacted with a Glycomimetic compound, in an amount and for a time sufficient to achieve a discernable diagnostic or therapeutic result. In the context of this invention, a therapeutic result would relate, for example, to the prevention of lung infections. In some conditions, therapeutic results would be associated with the inhibiting of *Pseudomonas* (such as *P. aeruginosa*) or its products (where inhibiting includes, for example, arresting the growth of or killing the bacteria or preventing colonization by the bacteria). As used herein, therapy or therapeutic results includes treatment or prevention.

Glycomimetic compounds of the present invention may be administered in a manner appropriate to the disease to be treated or prevented. Appropriate dosages and a suitable duration and frequency of administration may be determined by such factors as the condition of the patient, the type and severity of the patient's disease and the method of administration. In general, an appropriate dosage and treatment regimen provides the modulating agent(s) in an amount sufficient to provide treatment and/or prophylactic benefit. Within particularly preferred embodiments of the invention, a Glycomimetic compound may be administered at a dosage ranging from 0.001 to 1000 mg/kg body weight (more typically 0.01 to 1000 mg/kg), on a regimen of single or multiple daily doses. Appropriate dosages may generally be determined using experimental models and/or clinical trials. In general, the use of the minimum dosage that is sufficient to provide effective therapy is preferred. Patients may generally be monitored for therapeutic effectiveness using assays suitable for the condition being treated or prevented, which will be familiar to those of ordinary skill in the art. Glycomimetic compounds described herein may be administered in combination (i.e., simultaneously or sequentially) with another anti-bacterial compound. For example, a Glycomimetic compound may be administered in combination with tobramycin.

Glycomimetic compounds may also be used to target substances to *Pseudomonas* bacteria, e.g., *P. aeruginosa*. Such substances include therapeutic agents and diagnostic agents. Therapeutic agents may be a molecule, virus, viral component, cell, cell component or any other substance that can be demonstrated to modify the properties of a target cell so as to provide a benefit for treating or preventing a disorder or regulating the physiology of a patient. A therapeutic agent may also be a drug or a prodrug that generates an agent having a biological activity in vivo. Molecules that may be therapeutic agents may be, for example, polypeptides, amino acids, nucleic acids, polynucleotides, nucleosides, steroids, polysaccharides or inorganic compounds. Such molecules may function in any of a variety of ways, including as enzymes, enzyme inhibitors, hormones, receptors, antisense oligonucleotides, catalytic polynucleotides, anti-viral agents, anti-tumor agents, anti-bacterial agents, immunomodulating agents and cytotoxic agents (e.g., radionuclides such as iodine, bromine, lead, rhenium, homium, palladium or copper). Diagnostic agents include imaging agents such as metals and radioactive agents (e.g., gallium, technetium, indium, strontium, iodine, barium, bromine and phosphorus-containing compounds), contrast agents, dyes (e.g., fluorescent dyes and chromophores) and enzymes that catalyze a colorimetric or fluorometric reaction. In general, therapeutic and diagnostic agents may be attached to a Glycomimetic compound using a variety of techniques such as those described above. For targeting purposes, a Glycomimetic compound may be administered to a patient as described herein.

Glycomimetic compounds may also be used in vitro, e.g., within a variety of well known cell culture and cell separation methods. For example, a Glycomimetic compound may be immobilized on a solid support (such as linked to the interior surface of a tissue culture plate or other cell culture support) for use in immobilizing *Pseudomonas* bacteria or their products for screens, assays and growth in culture. Such linkage may be performed by any suitable technique, such as the methods described above, as well as other standard techniques. Glycomimetic compounds may also be used to facilitate cell identification and sorting in vitro, permitting the selection of such bacterial cells. Preferably, the Glycomimetic compound(s) for use in such methods is linked to a diagnostic agent which is a detectable marker. Suitable markers are well known in the art and include radionuclides, luminescent groups, fluorescent groups, enzymes, dyes, constant immunoglobulin domains and biotin. Within one preferred embodiment, a Glycomimetic compound linked to a fluorescent marker, such as fluorescein, is contacted with the cells, which are then analyzed by fluorescence activated cell sorting (FACS).

Such in vitro methods generally comprise contacting a sample (e.g., a biological preparation) with any one of the Glycomimetic compounds, and detecting the compound in the sample. If desired, one or more wash steps may be added to a method. For example, subsequent to contacting a sample with a Glycomimetic compound but prior to detection of the compound, the sample may be washed (i.e., contacted with a fluid and then removal of the fluid in order to remove unbound Glycomimetic compound). Alternatively, or in addition, a wash step may be added during the detection process. For example, if a Glycomimetic compound possesses a marker (a diagnostic agent) that can bind to a substance that is detectable, it may be desirable to wash the sample subsequent to contacting the sample with a detectable substance, but prior to the detection. As used herein, the phrase "detecting the compound (or agent) in the sample" includes detecting the compound (or agent) while it is bound to the sample, or detecting the compound (or agent) which was bound to the sample but after it has been separated from the sample.

The following Examples are offered by way of illustration and not by way of limitation.

EXAMPLES

Example 1

Synthesis of Glycomimetic 1

Reagents and solvents were used as received from commercial suppliers. Thin-layer chromatography (TLC) was performed using Analtech silica gel plates and visualized by UV light (254 nm) stain. Progress of the reactions was monitored by TLC or GC.

Preparation of B4 Derivatives

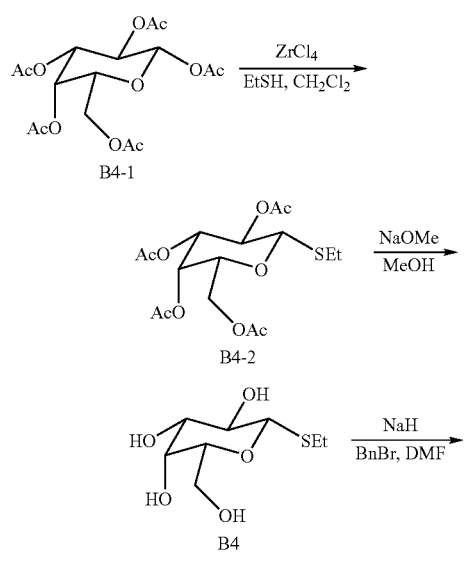

-continued

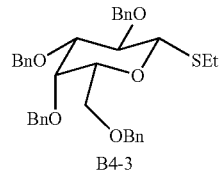

B4-3

Preparation of B4-2

A solution of B4-1 (150 g, 385 mmol) in $CH_2Cl_2$ (800 mL) was added slowly to a slurry of $ZrCl_4$ (85 g, 366 mmol) in $CH_2Cl_2$ (800 mL) at 0° C. After the reaction was stirred at 0° C. for 30 min, EtSH (32 mL, 423 mmol) was added and the reaction was complete within 2 h. The reaction was quenched by brine (500 mL). The layers were separated and the organic layer was washed with saturated aqueous $NaHCO_3$ (1×500 mL) and brine (1×500 mL), dried over $MgSO_4$, filtered, and concentrated to give an oily residue. This was dissolved in MTBE (300 mL) and the solution was diluted with heptane (1.2 L). After the resulting slurry had been stirred in an ice bath for 1 h, the mixture was filtered to provide compound B4-2 (143 g, 95%).

Preparation of B4

NaOMe (0.5 M in MeOH, 1.09 L, 545 mmol) was added to a solution of B4-2 (710 g, 392 mmol) in MeOH (4 L) at room temperature. After 2 h, Dowex 50wx8-200 resin (350 g) was added until the pH reached 3.5-4. The resin was filtered off and the filtrate was concentrated to an oily residue. This was dissolved in $CH_2Cl_2$ and concentrated again to give B4 as a solid (367 g, 90%).

Preparation of B4-3

A solution of B4 (10 g, 44.6 mmol) in anhydrous DMF (125 mL) was added to a suspension of NaH (14 g, 357 mmol, 60% in mineral oil) in anhydrous DMF (125 mL) at 0° C. After the reaction was stirred at room temperature for 30 min and then cooled to 0° C., BnBr (42 mL, 357 mmol) was added cautiously. The reaction was stirred at room temperature for 2 h and then cautiously quenched with MeOH (30 mL) while cooling in an ice bath. Water (200 mL) was added and the mixture was extracted with EtOAc (2×200 mL). The organic phase was washed with water (2×500 mL) and brine, dried over $MgSO_4$, and concentrated to an oily residue. Chromatographic purification on silica gel eluted with EtOAc/heptane (1:9) provided B4 (20.6 g, 79%).

Preparation of B2 Derivatives

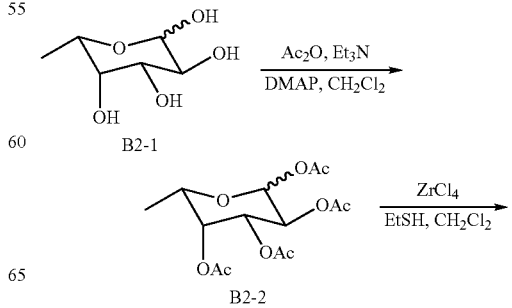

-continued

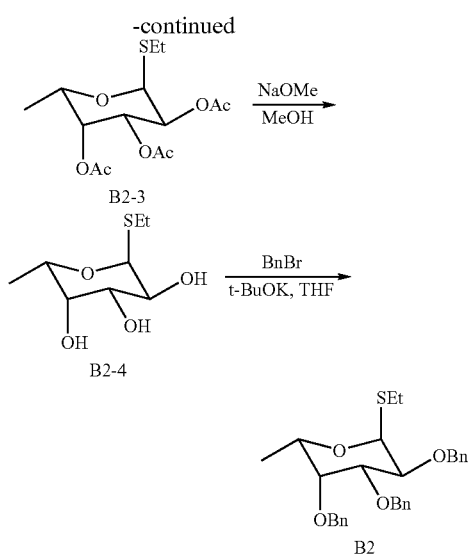

Preparation of B2-2

Triethylamine (6.8 L, 48.7 mol) was added to a solution of B2-1 (1 kg, 6.1 mol) and DMAP (74 g, 0.61 mol) in $CH_2Cl_2$ (12 L), followed by addition of $Ac_2O$ (3.46 L, 36.6 mol) at 0-10° C. The reaction was stirred at room temperature oversight and then quenched with water (25 L). The layers were separated. The organic phase was washed with water (25 L), saturated aqueous $NaHCO_3$ (2×10 L), and brine (10 L), dried over $MgSO_4$, and concentrated to provide crude B2-2 (2.1 kg, >quantitative).

Preparation of B2-3

A solution of B2-2 (1.5 kg, 3.01 mol) in $CH_2Cl_2$ (6 L) was added slowly to a slurry of $ZrCl_4$ (1 kg, 2.86 mol) in $CH_2Cl_2$ (1.2 L) at 0-5° C. After the reaction was stirred for 30 min, EtSH (351 mL, 3.16 mol) was added. The reaction was stirred at 0° C. Due to incomplete reaction, additional EtSH (3×3051 mL) was added during the first 30 h of the reaction. After 2 days the mixture was quenched with brine (7.5 L). The layers were separated and the organic layer was washed with saturated $NaHCO_3$ (6 L) and brine (6 L), dried over $MgSO_4$, and concentrated to give an oily residue. The residue was recrystallized from MTBE/heptane (1:3) to give a first crop of B2-3. The mother liquors were concentrated and the residue was purified by chromatography on silica gel eluted with EtOAc/heptane (2:8) to give a second crop. A total of 560 g of B2-3 (380% over two steps) was obtained.

Preparation of B2-4

NaOMe (25 wt % in MeOH, 119 mL, 519 mmol) was added slowly into a solution of B2-3 (579 g, 1.73 mol) in MeOH (2.3 L) at room temperature. After 1 h, Dowex 50wx8-200 resin (290 g) was added and the reaction was stirred for 30 min. The resin was filtered off and the filtrate was concentrated to afford solid B2-4 (360 g, quantitative).

Preparation of B2

A solution of B2-4 (360 g, 1.73 mol) in THF (3.5 L) was treated with potassium tert-butoxide (20 wt % in THF, 3.88 kg, 6.91 mol) at 0° C. After 30 min, BnBr (822 mL, 6.91 mol) was added. The reaction was stirred at room temperature for 2 h and then cooled to 10° C. After overnight stirring, the reaction was quenched with saturated aqueous $NH_4Cl$ (2 L) and then filtered through a pad of Celite. The filtrate was extracted with EtOAc (5.5 L). The organic phase was washed with brine (4 L) and concentrated. Chromatographic purification eluted with EtOAc/heptane (1:9) provided B2 (460 g, 560%).

Preparation of B5 Derivatives

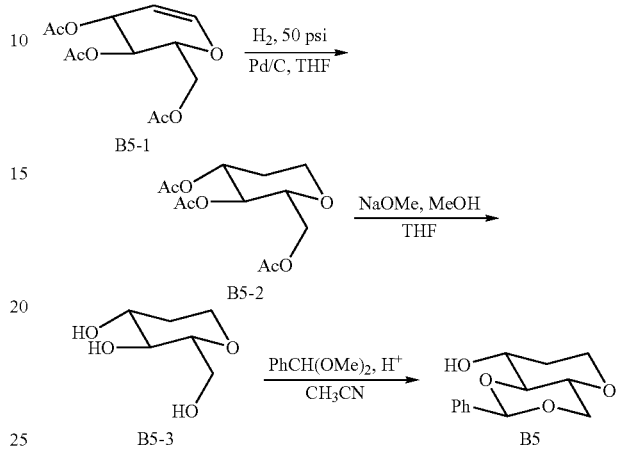

Preparation of B5-2

A suspension of B5-1 (184 g, 676 mmol, Aldrich) and Pd/C (10 wt %, 50% water wet; 19 g) in THF (800 mL) was hydrogenated at 50 psi overnight at room temperature. The catalyst was filtered off through a pad of Celite, the filter pad was washed with ethyl acetate, and the combined filtrate was concentrated. The residue was dissolved in ethyl acetate and the solution was then washed with water (250 mL), aqueous sodium bicarbonate (250 mL) and then brine (250 mL), dried over $MgSO_4$ and concentrated to give B5-2 as an oily residue (217 g, quantitative).

Preparation of B5-3

NaOMe (25 wt % in MeOH, 236 mL, 1.03 mol) was added slowly into a solution of B5-2 (189 g, 689 mmol) in MeOH (600 mL) at room temperature. After 2 h, Dowex 50wx8-200 (320 g) was added to adjust pH to 3.5-4. The resin was filtered off and the filtrate was concentrated. The residue was azeotroped with toluene and then with acetonitrile to give B5-3 (102 g, quantitative) as a waxy solid.

Preparation of B5

A suspension of B5-3 (69 g, 465 mmol) in $CH_3CN$ (1.2 L) was treated with benzaldehyde dimethyl acetal (76.9 mL, 512 mmol) and a solution of p-toluenesulfonic acid monohydrate (4.56 g, 24 mmol) in $CH_3CN$ (75 mL). After stirring at room temperature for 1 h, the reaction was heated to reflux for 1 h and then cooled to room temperature and neutralized with $Et_3N$ (3 mL). The mixture was concentrated and the residue was dissolved with EtOAc (800 mL). The solution was washed with water (500 mL) and then brine (500 mL), dried over $MgSO_4$, and concentrated to give a crude product. This was dissolved in ethyl acetate (100 mL) at 70° C. and then treated with heptane (270 mL, in 50 mL portions). The mixture was cooled to room temperature and filtered to give a first crop of B5. Chromatographic purification of the mother liquors on silica gel eluted with EtOAc/heptane (3:7) gave a second crop. A total of 88 g of B5 (80%) was obtained.

Preparation of Glycomimetic 1

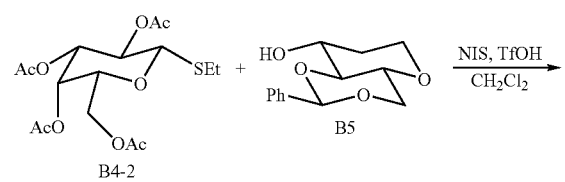

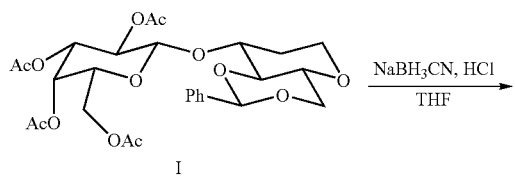

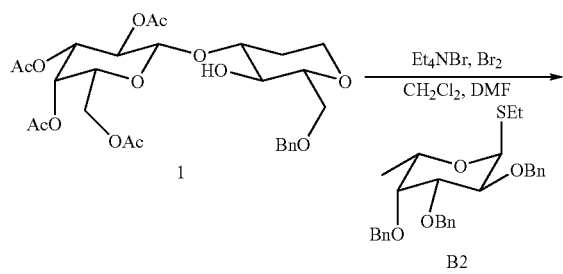

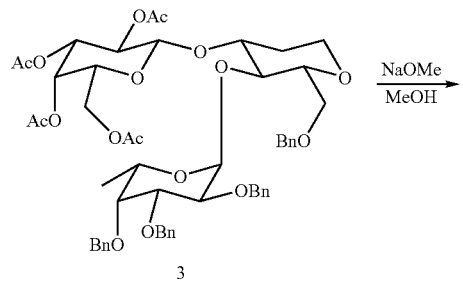

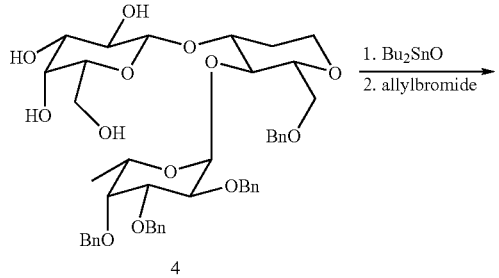

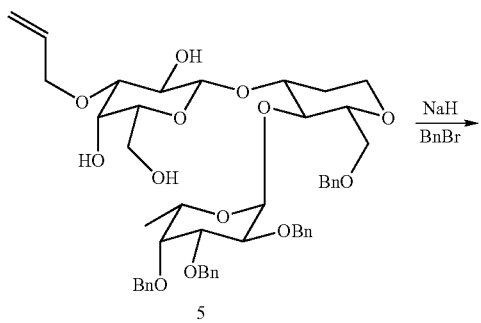

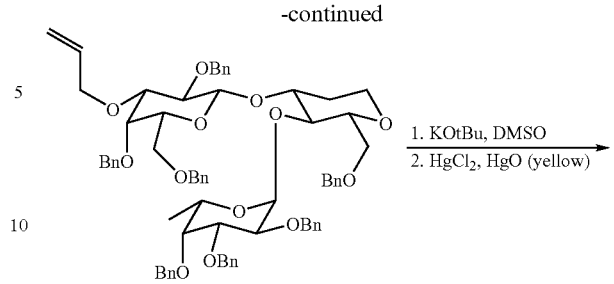

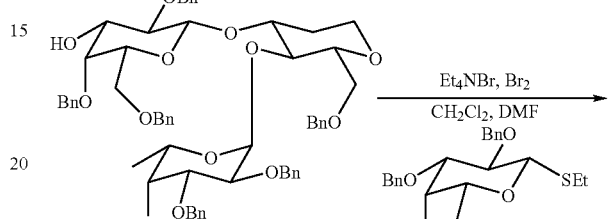

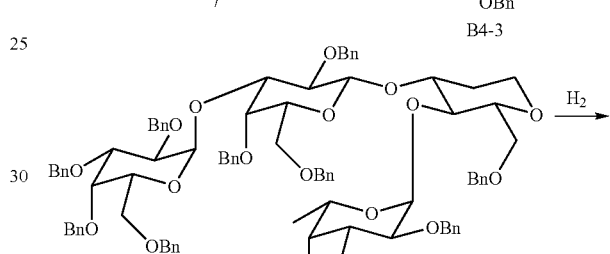

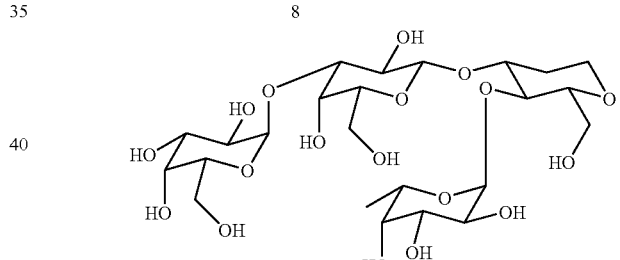

Glycomimetic 1

Preparation of Compound 1

A suspension of B5 (20 g, 87.4 mmol), B4-2 (40 g, 101.6 mmol), and N-iodosuccinimide (25 g, 110.1 mmol) in $CH_2Cl_2$ (230 mL, anhydrous) was treated with trifluoromethanesulfonic acid (0.15 M in $CH_2Cl_2$, about 2 mL; freshly prepared before use) at 0° C. until the color changed from light red brown to dark brown. The reaction was stirred in an ice bath for 40 min and then quenched with aqueous $Na_2CO_3$ (80%, 100 mL) to pH 9. After dilution with $CH_2Cl_2$ (100 mL) and water (100 mL), the layers were separated. The organic phase was washed with aqueous $Na_2S_2O_3$ (100%, 370 mL) and then brine (100 mL), dried over $Na_2SO_4$, and concentrated. Chromatographic purification on silica gel eluted with MTBE/heptane (6:4) gave 1 (40.8 g, 810%) as a foam.

Preparation of Compound 2

A solution of $NaBH_3CN$ (42 g, 670 mmol) in anhydrous THF (280 mL) was added into a solution of compound 1 (38 g, 67 mmol) in anhydrous THF (70 mL) at room temperature. Molecular sieves (3 Å, powder, dried; 30 g) were then added and the reaction mixture was stirred at room temperature for 30 min before being cooled to 0° C. HCl (in anhydrous $Et_2O$, prepared before use; ~90 mL) was added slowly until the complete consumption by TLC of compound 1. Solid $Na_2CO_3$ (35 g) was added portionwise into the reaction with cooling of an ice bath and the slurry was stirred for 10 min before filtering through a pad of Celite. The filtrate was diluted with EtOAc (300 mL), washed with saturated aqueous $NaHCO_3$ (100 mL) and brine (100 mL), and concentrated to a yellow oil. This residue was partitioned between toluene (400 mL) and water (200 mL) but three layers formed. The layers were separated and the middle layer was repeatedly partitioned between toluene (6×400 mL) and water (6×100 mL). The combined organic layers were concentrated to give crude 2 (35 g). Chromatographic purification on silica gel eluted with EtOAc/heptane (6:4) provided 2 (26 g, 680%) as an oily foam.

Preparation of Compound 3

Part 1: $Br_2$ (distilled over $P_2O_5$, 1.8 mL, 34.8 mmol) was added dropwise to a solution of B2 (13.9 g, 29 mmol) in anhydrous $CH_2Cl_2$ (30 mL) at 0° C. After the reaction had been stirred in an ice bath for 40 min, cyclohexene (4 mL) was added until the color changed to a persistent yellow.

Part 2: Compound 2 (11 g, 19.4 mmol) was dissolved in anhydrous $CH_2Cl_2$ (80 mL), followed by addition of $Et_4NBr$ (dried at 200° C. for 2 h under $N_2$; 6.1 g, 29 mmol), anhydrous DMF (50 mL), and molecular sieves (4 Å powder, dried; 12 g). After the reaction mixture had been stirred at room temperature for 30 min, the solution from part 1 was added. The reaction mixture was stirred for 40 h at room temperature and then diluted with EtOAc (100 mL) and filtered through a pad of Celite. The filtrate was washed with aqueous $Na_2S_2O_3$ (10%, 100 mL), water (100 mL), and then brine (100 mL), dried over $Na_2SO_4$, and concentrated. Chromatographic purification on silica gel eluted with EtOAc/heptane (1:1) gave 3 (15 g, 78%) as an oily foam.

Preparation of Compound 4

NaOMe (0.5 M in MeOH, 4.6 mL, 2.24 mmol) was added to a solution of compound 3 (11 g, 11.2 mmol) in MeOH (30 mL) at room temperature. After 3 h, AcOH (1 mL) was added and pH reached 4. The mixture was concentrated to give crude 4 (9.2 g, quantitative), used without additional purification in the next step.

Preparation of Compound 5

A mixture of compound 4 (9.2 g, 12.3 mmol) and dibutyltin oxide (3.92 g, 15.8 mmol) in anhydrous MeOH (150 mL) was heated to reflux for 4 h and then the reaction was evaporated to dryness. The residue was dissolved in toluene (150 mL, anhydrous) in a dry flask. Tetrabutylammonium bromide (3.65 g, 7.91 mmol) and allyl bromide (1.6 mL, 18.1 mmol) were added. The reaction mixture was heated to reflux for 4 h, cooled and then concentrated. The residue was purified by chromatography on silica gel eluted with EtOAc/$CH_2Cl_2$ (7:3) to give 5 (6.4 g, 67% over two steps).

Preparation of Compound 6

A solution of compound 5 (6.3 g, 7.35 mmol) in anhydrous DMF (30 mL) was added into a suspension of NaH (1.47 g, 36.8 mmol, 60% in mineral oil) in anhydrous DMF (30 mL) at 0° C. After the reaction had been stirred at room temperature for 30 min, it was cooled to 0° C. and BnBr (3.95 mL, 33.1 mmol) was added. The reaction was stirred at room temperature for 2 h and then quenched with MeOH (1.5 mL) in an ice bath. Water (20 mL) and ice cold aqueous HCl (1 M, 100 mL) were added, followed by extraction with $CH_2Cl_2$ (200 mL). The layers were separated and the organic phase was washed with water (200 mL), ice cold saturated aqueous $NaHCO_3$ (100 mL), and brine, dried over $Na_2SO_4$, and concentrated. Chromatographic purification on silica gel eluted with EtOAc/heptane (1:4) provided 6 (6.36 g, 780%).

Preparation of Compound 7

KOtBu (1.57 g, 14.0 mmol) was added to a solution of compound 6 (6.3 g, 5.59 mmol) in DMSO (40 mL) at room temperature. The slurry was heated to 100° C. in a pre-heated oil bath for 2 h. After the reaction had been cooled to room temperature, $CH_2Cl_2$ (150 ML) and water (100 mL) were added. The layers were separated and the aqueous phase was extracted with $CH_2Cl_2$ (2×150 mL). The combined organics were washed with water (3×100 mL) and then brine (100 mL), dried over $Na_2SO_4$, and concentrated to a residue (6.4 g). This was dissolved with acetone (40 mL) and water (4 mL), HgO (yellow; 3.3 g, 15.1 mmol) was added followed by a solution of $HgCl_2$ (anhydrous; 3.3 g, 12.3 mmol) in acetone (40 mL) and water (4 mL) dropwise. After 30 min, the mixture was filtered through a pad of Celite and the filtrate was concentrated. The residue was partitioned between $CH_2Cl_2$ (200 mL) and saturated aqueous NaI (30 mL). The organic layer was washed with water (100 mL) and then brine, dried over $Na_2SO_4$, and concentrated. Chromatographic purification on silica gel eluted with EtOAc/heptane (1:4) provided 7 (4.35 g, 720%) as a yellow oil.

Preparation of Compound 8

Part 1: $Br_2$ (distilled over $P_2O_5$, 0.39 mL, 7.59 mmol) was added dropwise to a solution of B4-3 (4.03 g, 6.9 mmol) in anhydrous $CH_2Cl_2$ (10 mL) at 0° C. After the reaction had been stirred in an ice bath for 40 min, cyclohexene (1 mL) was added until the color changed to a persistent yellow.

Part 2: Compound 7 (3.75 g, 3.45 mmol) was dissolved in anhydrous $CH_2Cl_2$ (25 mL) and then $Et_4NBr$ (dried at 200° C. for 2 h under $N_2$, 1.45 g, 6.9 mmol), anhydrous DMF (15 mL), and molecular sieves (4 Å powder, dried; 4 g) were added. After this mixture had been stirred at room temperature for 30 min, the solution from part 1 was added. The reaction was stirred for 60 h at room temperature and then diluted with EtOAc (50 mL) and filtered through a pad of Celite. The filtrate was washed with aqueous $Na_2S_2O_3$ (10%, 50 mL), water (30 mL), and then brine (30 mL), dried over $Na_2SO_4$, and concentrated. Chromatographic purification on silica gel eluted with EtOAc/heptane (1:3) gave 8 (3.94 g, 71%) as a foam.

Preparation of Glycomimetic 1

A suspension of 8 (3.9 g, 2.42 mmol) and $Pd(OH)_2$/C (20 wt %, 50% water wet; 2 g) in MeOH (150 mL), 1,4-dioxane (15 mL), and AcOH (5 mL) was hydrogenated under 60 psi at room temperature for 20 h. The mixture was filtered through a pad of Celite and the filtrate was concentrated. Chromatographic purification on silica gel eluted with $CH_2Cl_2$/MeOH/ $H_2O$ (10:9:1) gave Glycomimetic 1 (1.05 g, 70%) as a white solid.

Example 2

Synthesis of Glycomimetic (Compound XXVIII)

Figure 3A:
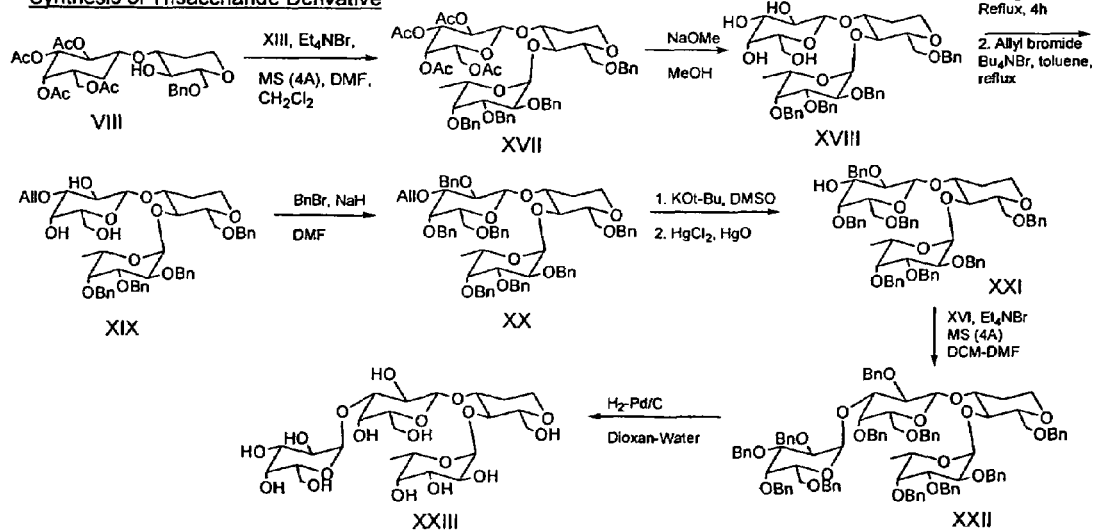
FIGS. 3A and 3B are diagrams illustrating the synthesis of glycomimetic compounds.
Figure 3B:
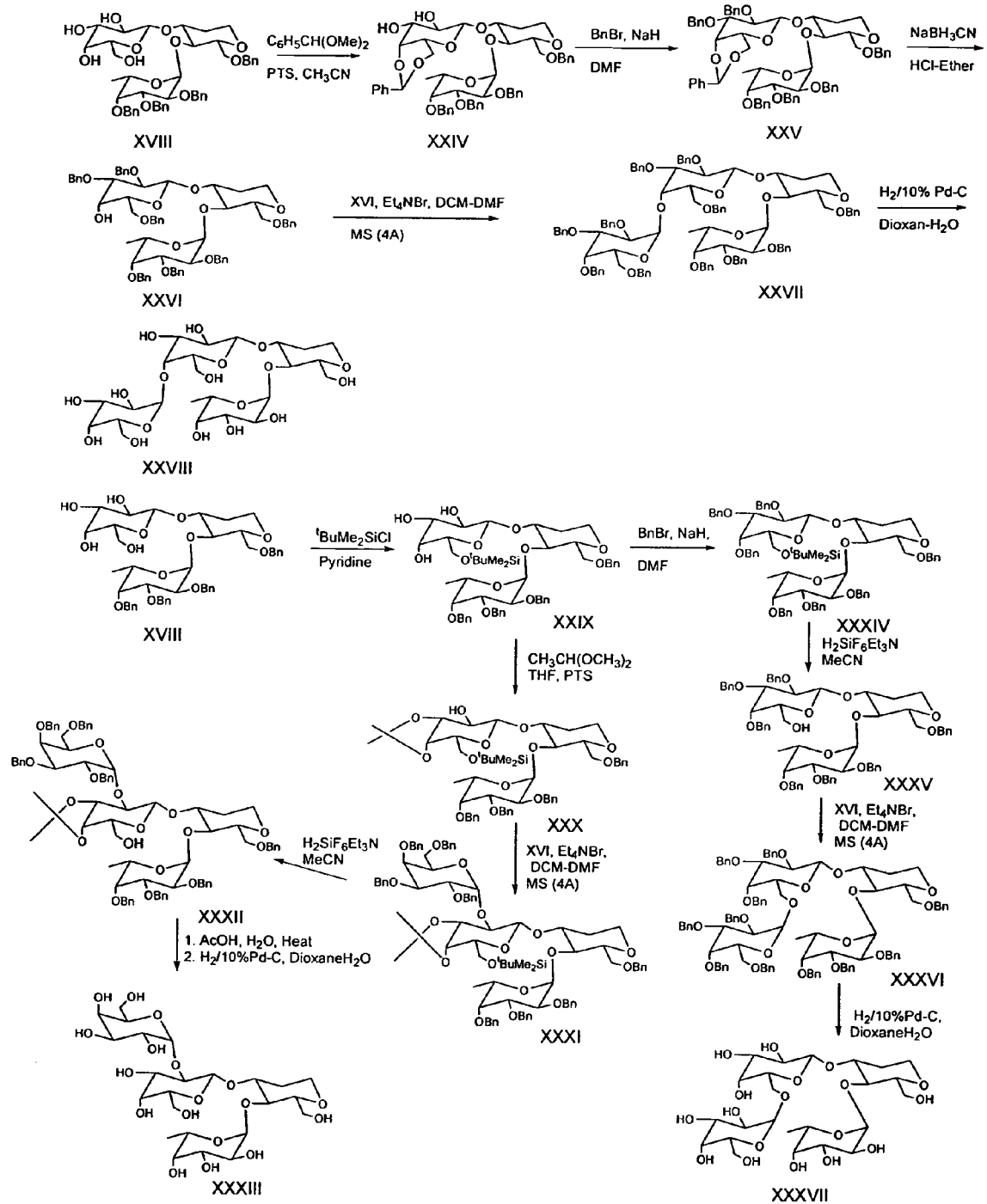
Figure 4:
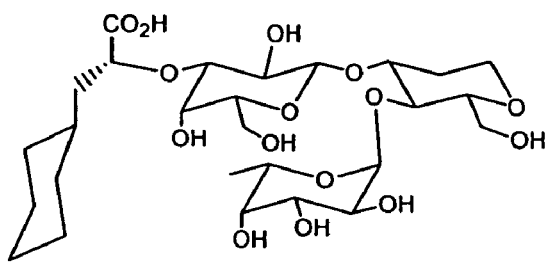
FIG. 4 depicts the structures of three of the compounds (Compound A, Compound B, and Glycomimetic 1) used in one or more of the lectin assays described herein.
Figure 4:
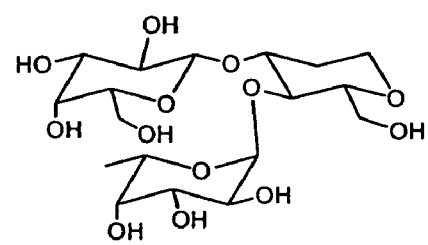
Figure 4:
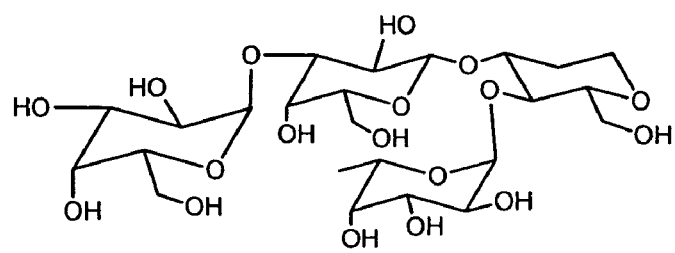
Figure 5:
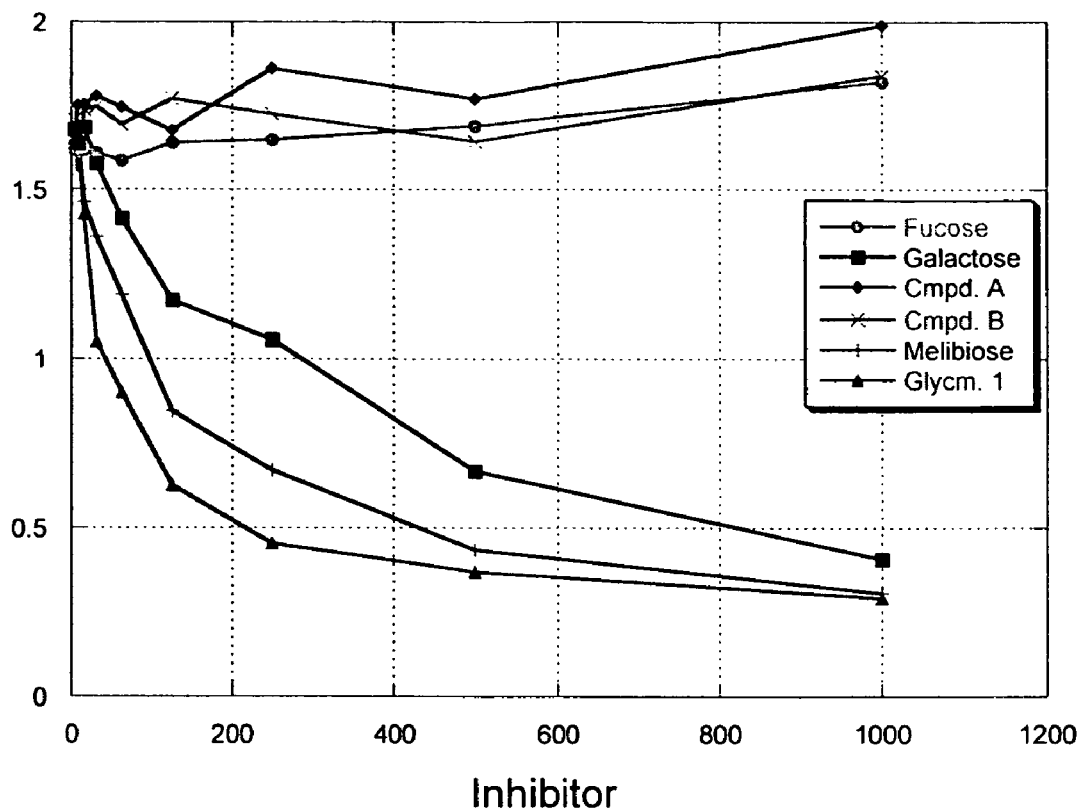
FIG. 5 graphically illustrates the inhibition of PA-IL lectin by Glycomimetic 1 ("Glycm 1"). PA-IL lectin is a galactose-binding lectin and is inhibited by galactose, Melibiose (Galα1-6Gal), and Glycomimetic 1; but not by fucose, Compound A or Compound B.
Figure 6:
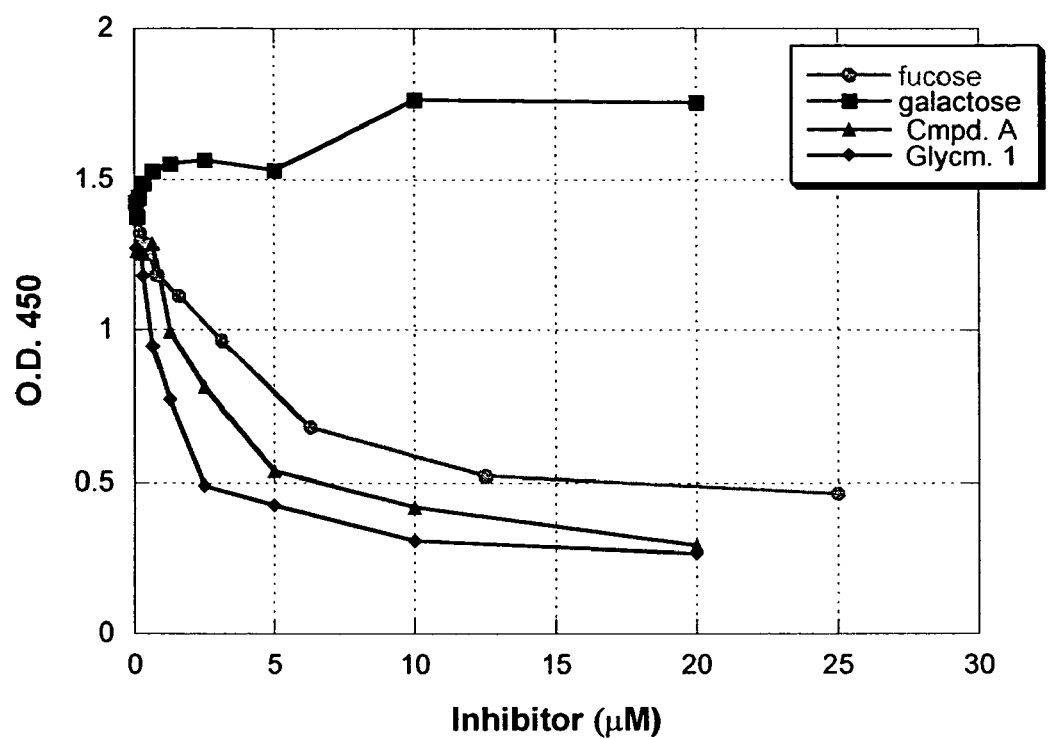
FIG. 6 graphically illustrates inhibition of the PA-IIL Lectin. The fucose binding lectin, PA-IIL is inhibited by fucose, Compound A and Glycomimetic 1; but not by galactose.
Figure 7:
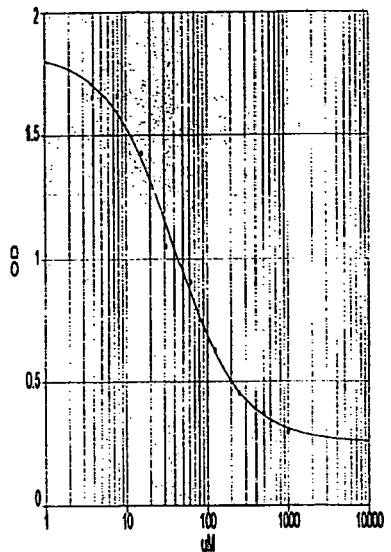
FIG. 7 shows the determination of IC$_{50}$ value for Glycomimetic 1 for inhibition of PA-IL. Glycomimetic 1 inhibits the galactose-binding lectin, PA-IL about 4 to 5 times better than galactose; whereas, fucose is inactive.
Figure 7:
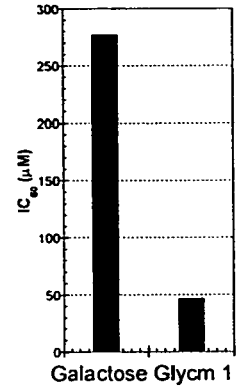
Figure 8:
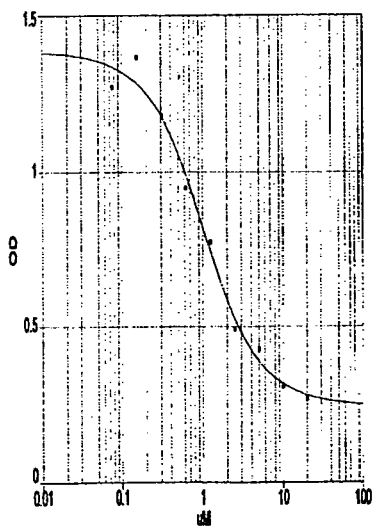
FIG. 8 shows the IC$_{50}$ determination of Glycomimetic 1 for inhibition of PA-IIL. Glycomimetic 1 inhibits the fucose-binding lectin, PA-IIL about 4 to 5 times better than fucose; while galactose is inactive.
Figure 8:
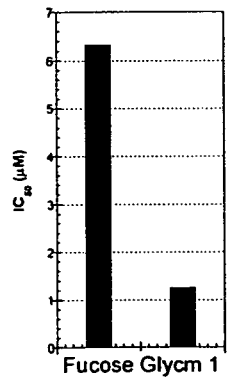
Figure 9:
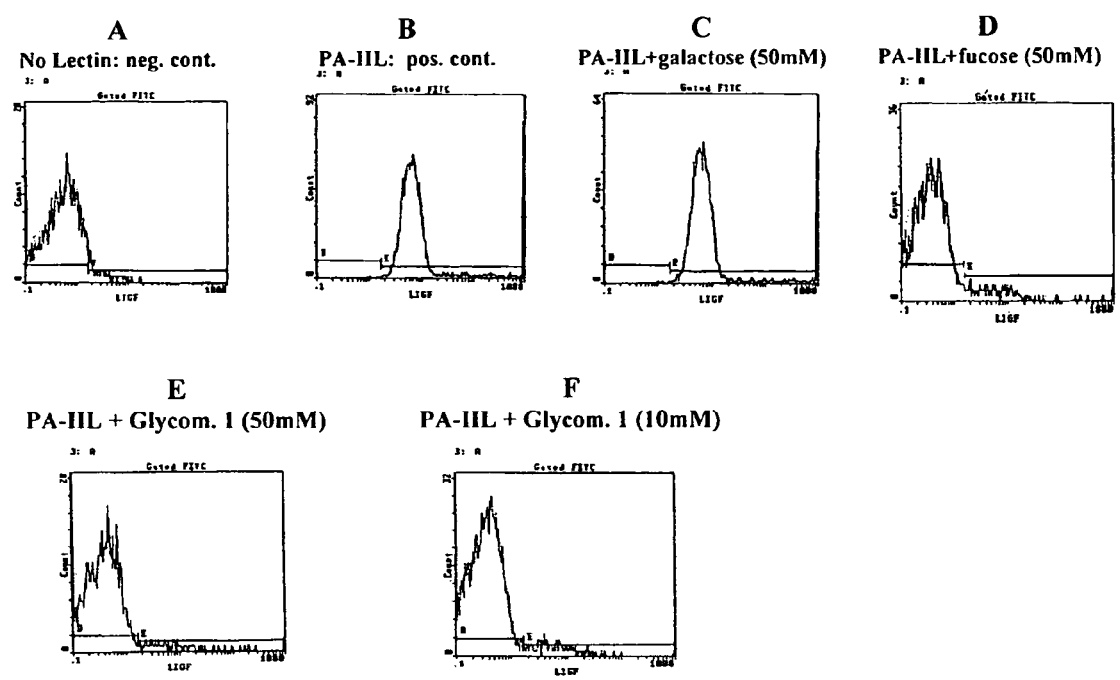
FIG. 9 illustrates the inhibition of PA-IIL binding to human epithelial cells. Human buccal epithelial cells are incubated with biotinylated PA-IIL lectin followed by detection of bound lectin with fluorescein-labeled streptavidin. Fluorescently labeled cells are quantified by fluorescent-activated cell sorting (B). Incubation of the PA-IIL lectin with fucose (D) or Glycomimetic 1 (E and F) inhibits binding to the cell surface. Galactose (C) has no effect.

Chemical structures are depicted in FIGS. 3A-3B.

Synthesis of intermediate XIVV: To a solution of compound XVIII (0.8 g) in acetonitrile (10 ml) is added benzaldehydedimethylacetal (0.5 g) and p-toluenesulfonic acid (0.2 mg) and the mixture is stirred at room temperature for 6 h.

Triethylamine (0.2 ml) is added and the reaction mixture is stirred at room temperature for 5 min. Solvent is evaporated off and the residue is purified by column chromatography (silica gel) to give intermediate XVIV.

Synthesis of intermediate XXV: To a solution of compound XVIV (0.5 g) in DMF (5 ml) is added sodium hydride (0.1 g, 60% suspension in oil) with stirring. Benzyl bromide (0.2 ml) is added drop wise to the above reaction mixture and stirred at room temperature for 16 h. Methanol (0.5 ml) is added with stirring and the reaction mixture is concentrated to dryness. Dichloromethane (50 ml) is added and the organic layer is washed successively with cold 1N HCl cold sodium bicarbonate solution and cold water. Organic layer is dried (sodium sulfate), filtered and concentrated to dryness. Residue is purified by column chromatography (silica gel) to give compound XXV.

Synthesis of intermediate XXVI: To a cold solution of XXV (0.4 g) in THF (5 ml) is added sodiumcyanoborohydride (0.1 g). A cold solution of HCl in ether is added drop wise until effervescence ceases (pH 2-3). Reaction mixture is diluted with ether (50 ml) and washed successively with a cold aqueous solution of sodium bicarbonate, and cold water. Solvent is evaporated off and the residue is purified by column chromatography (silica gel) to give compound XXVI.

Synthesis of intermediate XXVII: To a solution of compound XXVI (0.1 g) in dichloromethane-DMF (2 ml) is added molecular sieves (4A, 0.1 g) and tetraethyl ammonium bromide (0.05 g) and the reaction mixture is stirred for 1 h at room temperature under argon. To this reaction mixture is added compound XVI (0.1 g) and the reaction mixture is stirred at room temperature for 48 h under argon. Reaction mixture is diluted with dichloromethane (10 ml) and washed successively with cold saturated sodium bicarbonate solution and water; then dried (sodium sulfate), filtered and concentrated to dryness. The residue is purified by column chromatography (silica gel) to give compound XXVII.

Synthesis of compound XXVIII: To a solution of compound XXVII (0.06 g) in dioxane-water (5 ml, 6:1) is added acetic acid (10 drops) and 10% Pd—C (0.06 g). The reaction mixture is vigorously shaken under hydrogen for 20 h. Reaction mixture is filtered through a bed of celite and the solvent is evaporated off. Residue is purified by passing through a column of sephadex G-10 to give compound XXVIII.

Example 3

Synthesis of Glycomimetic (Compound XXXIII)

Chemical structures are depicted in FIGS. 3A-3B.

Synthesis of intermediate XXIX: To a solution of compound XVIII (2 g) in pyridine (20 ml) is added tert-butyldimethylsialylchloride (0.6 g) and the solution is stirred at room temperature for 16 h. Solvent is evaporated off and the residue is purified by column chromatography (silica gel) to give compound XXIX.

Synthesis of intermediate XXX: To a suspension of compound XXIX (1 g) in α,α-dimethoxy propane (10 ml) is added camphorsulfonic acid (0.2 g) and the reaction mixture is stirred at room temperature for 16 h. Triethylamine (0.2 ml) is added and the solvent is evaporated off. The residue is purified by column chromatography (silica gel) to give compound XXX.

Synthesis of intermediate XXXI: Compound XXX (0.8 g) is reacted with compound XVI (0.8 g) in the same way as described in Example 2 to give compound XXXI.

Synthesis of intermediate XXXII: To a solution of compound XXXI (0.5 g) in acetonitrile (5 ml) is added triethylamine (0.1 ml) and a solution of $H_2SiF_6$ (0.5 ml, 35%) in acetonitrile (1 ml). After 2 h, the reaction mixture is diluted with dichloromethane (50 ml) and washed with cold saturated solution of sodium bicarbonate and cold water, then dried (sodium sulfate), filtered, and concentrated to dryness. The residue is purified by column chromatography (silica gel) to give compound XXXII.

Synthesis of compound XXXIII: A solution of compound XXXII (0.2 g) in 60% acetic acid in water is heated at 60° C. for 1 h. Solvent is evaporated off and the crude product is dissolved in dioxan-water (5 ml, 6:1). Acetic acid (10 drops) is added followed by 10% Pd—C. The suspension is shaken under hydrogen for 24 h, filtered (Celte bed) and concentrated to dryness. The residue is purified by passing through a column of sephadex G-10 to give compound XXXIII.

Example 4

Synthesis of Glycomimetic (Compound XXXVII)

Chemical structures are depicted in FIGS. 3A-3B.

Synthesis of intermediate XXXIV: A solution of XXIX (1 g) in DMF is treated with NaH (0.14 g) and benzyl bromide (0.4 ml) in same way as described in Example 2 and purified by column chromatography (silica gel) to give compound XXXIV.

Synthesis of intermediate XXXV: Compound XXXIV (1 g) is treated with $H_2SiF_6$ in the same way as described in Example 3 to give compound XXXV.

Synthesis of intermediate XXXVI: Intermediate XXXV (0.5 g) is reacted with intermediate XVI (0.4 g) as described in Example 2 to give compound XXXVI.

Synthesis of compound XXXVII: Intermediate XXXVI (0.3 g) is hydrogenated as described in Example 2 and purified by sephadex G-10 to give compound XXXVII.

Example 5

Assay for PA-IL Antagonist Activity

Wells of a microtiter plate (plate 1) are coated with PA-IL (Sigma-Aldrich, St. Louis, Mo.) by incubation for 2 hrs at 37° C. The wells are then blocked for 2 hrs by the addition of 1% bovine serum albumin (BSA) diluted in TBS-Ca (50 mM Tris HCl, 150 mM NaCl, 2 mM $CaCl_2$ pH 7.4) mixed 1:1 v/v with Stabilcoat (Surmodics, Eden Prairie, Minn.). In a second low-binding round-bottom microtiter plate (plate 2), test antagonists are serial diluted in 1% BSA in TBS-Ca/Stabilcoat (60 μl/well). Preformed conjugates of α-galactose-PM-biotin (GlycoTech Corp, Gaithersburg, Md.) mixed with streptavidin-HRP (KPL Labs, Gaithersburg, Md.) are added to each well of plate 2 (60 μl/well of 2 μg/ml). Plate 1 is then washed with TBS-Ca and 100 μl/well are transferred from plate 2 to plate 1. After incubation at room temperature for 2 hrs, plate 1 is washed and 100 μl of TMB reagent (KPL Labs, Gaithersburg, Md.) is added to each well. After incubation for 5 minutes at room temperature, the reaction is stopped by adding 100 μl/well of 1M $H_3PO_4$ and the absorbance of light at 450 nm is determined by a microtiter plate reader.

Example 6

Assay for PA-IIL Antagonist Activity

Wells of a microtiter plate (plate 1) are coated with PA-IIL (Dr. Wimmerova, Masaryk University, Brno, Czech Republic) by incubation for 2 hrs at 37° C. The wells are then blocked for 2 hrs by the addition of 1% bovine serum albumin (BSA) diluted in TBS-Ca (50 mM Tris HCl, 150 mM NaCl, 2 mM $CaCl_2$ pH 7.4) mixed 1:1 v/v with Stabilcoat (Surmodics, Eden Prairie, Minn.). In a second low-binding round-bottom microtiter plate (plate 2), test antagonists are serial diluted in 1% BSA in TBS-Ca/Stabilcoat (60 μl/well). Preformed conjugates of fucose-PAA-biotin (GlycoTech Corp, Gaithersburg, Md.) mixed with streptavidin-HRP (KPL Labs, Gaithersburg, Md.) are added to each well of plate 2 (60 μl/well of 2 μg/ml). Plate 1 is then washed with TBS-Ca and 100 μl/well are transferred from plate 2 to plate 1. After incubation at room temperature for 2 hrs, plate 1 is washed and 100 μl of TMB reagent (KPL Labs, Gaithersburg, Md.) is added to each well. After incubation for 5 minutes at room temperature, the reaction is stopped by adding 100 μl/well of 1M $H_3PO_4$ and the absorbance of light at 450 nm is determined by a microtiter plate reader.

Example 7

Assay for Inhibition of PA-I or PA-II Lectin Binding to Buccal Cells

Obtain sample of buccal cells by scraping inside of cheek and collecting in 2 mls PBS. Spin cells at 400 g for 7 minutes to generate cell pellet. Discard supernatant. Resuspend in cold TBS-Ca (50 mM Tris HCl, 150 mM NaCl, 2 mM $CaCl_2$ pH 7.4) to cell concentration of $10^6$ cells/ml. Aliquot 0.1 ml to each tube. Add biotinylated PA-I or PA-II to tubes (5 μ/well of 1.0 mg/ml lectin). Add inhibitors to tubes (5 μl at desired concentration). Incubate on ice for 30 minutes. Wash cells once by adding 400 μl of cold TBS-Ca to each tube and spinning at 400 g for 7 minutes. Discard supernatant. Resuspend cells in 100 μl of cold TBS-Ca. Add streptavidin-FITC (2 μl/tube of 1 mg/ml, KPL Labs, Gaithersburg, Md.). Incubate 30 minutes on ice. Wash cells once by adding 400 μl of cold TBS-Ca to each tube and spinning at 400 g for 7 minutes. Discard supernatant. Resuspend cells in 500 μl of cold TBS-Ca. Analyze in flow cytometer.

From the foregoing it will be appreciated that, although specific embodiments of the invention have been described herein for purposes of illustration, various modifications may be made without deviating from the spirit and scope of the invention.

The invention claimed is:

1. A compound or physiologically acceptable salt thereof with the formula:

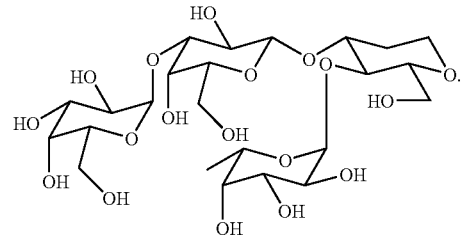

2. The compound or physiologically acceptable salt thereof according to claim 1 wherein the compound or physiologically acceptable salt thereof is in combination with a pharmaceutically acceptable carrier or diluent.

* * * * *

UNITED STATES PATENT AND TRADEMARK OFFICE
CERTIFICATE OF CORRECTION

PATENT NO. : 7,517,980 B2
APPLICATION NO. : 11/501464
DATED : April 14, 2009
INVENTOR(S) : John L. Magnani et al.

It is certified that error appears in the above-identified patent and that said Letters Patent is hereby corrected as shown below:

Title page, Item 54 and Col. 1, line 5
"GLYCOMIMETRIC INHIBITORS OF THE PA-IL LECTIN, PA-IIL LECTIN OR BOTH THE LECTINS FROM *PSEUDOMONAS*" should read as --GLYCOMIMETIC INHIBITORS OF THE PA-IL LECTIN, PA-IIL LECTIN OR BOTH THE LECTINS FROM *PSEUDOMONAS*--.

Title page, Item 56
"4,876,199 A 10/1989 Hakamori 530/387" should read as --4,876,199 A 10/1989 Hakomori 530/387--

Item 56
"6,309,639 B1 10/2001 Cummings et al. 434/143.1" should read as --6,309,639 B1 10/2001 Cummings et al. 424/143.1--

Item 56
"6,492,332 B1 12/2002 Demopulos et al. 514/12" should read as --6,492,332 B1 10/2002 Demopulos et al. 514/12--

Item 56
"WO WO 95/00527 11/1995" should read as --WO WO 95/00527 1/1995--

Item 56
"Banteli, R. et al., "Potent E-Selectin Antagonist," *Helvectica Chimica Acta 83*(11): 2893-2907, 2000" should read as --Banteli, R. et al., "Potent E-Selectin Antagonists," *Helvetica Chimica Acta 83*(11): 2893-2907, 2000--

Item 56
"Berg et al., "A Carbohydrate Domain Ceommon" should read as --Berg et al., "A Carbohydrate Domain Common--

Item 56
"Berg et al., "The Cutaneous Lymphocyte Antigen Is a Skin Lymphocyte Homing Receptor for the Vascular Lectin Endothelial Cell-Leukocyte Adhesion Molecular 1" should read as --Berg et al., "The Cutaneous Lymphocyte Antigen Is a Skin Lymphocyte Homing Receptor for the Vascular Lectin Endothelial Cell-Leukocyte Adhesion Molecule 1--

Item 56
"Broquet et al., "Effect of Desipramine on a Glycoprotein Sialytransferase Activity" should read as --Broquet et al., "Effect of Desipramine on a Glycoprotein Sialyltransferase Activity--

Item 56
"Duijvetjin et al.," should read as --Duijvestijn et al.,--

CERTIFICATE OF CORRECTION (continued)
U.S. Pat. No. 7,517,980 B2

Item 56
"Fukushi et al., "Novel Fucolipidis Accumulating" should read as --Fukushi et al., "Novel Fucolipids Accumulating--

Item 56
"Handa et al.,...Sulfated Glycans Moldulate this" should read as --Handa et al., Sulfated Glycans Modulate this--

Item 56
"Ward and Mulligan, "Blocking of adhesion molecules in vivo as anti-inflammatory therapy," *Immunology I*:165-171, 1994" should read as --Ward and Mulligan, "Blocking of adhesion molecules in vivo as anti-inflammatory therapy," *Immunology 1*:165-171, 1994--

Signed and Sealed this

Ninth Day of February, 2010

David J. Kappos
*Director of the United States Patent and Trademark Office*